(12) United States Patent
Luebcke

(10) Patent No.: US 10,406,383 B2
(45) Date of Patent: Sep. 10, 2019

(54) APPARATUS FOR TREATMENT OF DERMATOLOGICAL CONDITIONS

(75) Inventor: Peter Luebcke, Royston (GB)

(73) Assignee: CAREWEAR CORP., Reno, NV (US)

( * ) Notice: Subject to any disclaimer, the term of this patent is extended or adjusted under 35 U.S.C. 154(b) by 939 days.

(21) Appl. No.: 13/137,043

(22) Filed: Jul. 18, 2011

(65) Prior Publication Data

US 2011/0269693 A1 Nov. 3, 2011

Related U.S. Application Data

(62) Division of application No. 11/664,098, filed as application No. PCT/GB2005/050181 on Oct. 11, 2005, now abandoned.

(30) Foreign Application Priority Data

Oct. 11, 2004 (GB) .................................. 0422525.6

(51) Int. Cl.
*A61N 7/00* (2006.01)

(52) U.S. Cl.
CPC ........ *A61N 7/00* (2013.01); *A61N 2007/0008* (2013.01); *A61N 2007/0073* (2013.01); *A61N 2007/0078* (2013.01)

(58) Field of Classification Search
USPC ........................................ 600/407, 437, 439
See application file for complete search history.

(56) References Cited

U.S. PATENT DOCUMENTS

| | | |
|---|---|---|
| 4,767,402 A | 4/1988 | Kost et al. |
| 5,186,162 A | 2/1993 | Talish et al. |
| 5,507,790 A | 4/1996 | Weiss |
| 5,618,275 A * | 4/1997 | Bock .............................. 604/290 |
| 5,665,053 A | 9/1997 | Jacobs et al. |
| 6,030,374 A | 2/2000 | McDaniel et al. |

(Continued)

FOREIGN PATENT DOCUMENTS

| | | |
|---|---|---|
| CN | 1082406 | 2/1994 |
| CN | 2246523 | 2/1997 |

(Continued)

OTHER PUBLICATIONS

"Dual Frequency Array Transducer for Ultrasonic-Enhanced Transcranial Thrombolysis" by T. Azuma et al. IEEE Ultrasonics Symposium. vol. 1. Oct. 5-8, 2003.*

(Continued)

*Primary Examiner* — Baisakhi Roy
*Assistant Examiner* — Jason M Ip
(74) *Attorney, Agent, or Firm* — Stinson LLP

(57) ABSTRACT

This invention relates to ultrasound delivery apparatus comprising flexible arrays of transducers and to methods and topical compositions for the treatment of skin, in particular for the treatment of cosmetic skin conditions and to improve the appearance of sun damaged and/or aged skin; the invention further relates to the use of such apparatus and compositions in methods of treating skin, which methods may incorporate the application of ultrasound. The composition may comprise one or more anti-gfycation agent, one or more anti-oxidant, a dermatologically acceptable excipient and optionally one or more substance capable of inducing expression of a molecular chaperone.

28 Claims, 6 Drawing Sheets

(56) References Cited

U.S. PATENT DOCUMENTS

| | | | |
|---|---|---|---|
| 6,113,559 | A | 9/2000 | Klopotek et al. |
| 6,200,266 | B1 | 3/2001 | Shokrollahi et al. |
| 6,234,990 | B1 | 5/2001 | Rowe et al. |
| 6,565,520 | B1 | 5/2003 | Young |
| 6,585,763 | B1* | 7/2003 | Keilman et al. ............. 623/1.42 |
| 6,613,005 | B1 | 9/2003 | Friedman et al. |
| 7,273,457 | B2 | 9/2007 | Penner |
| 7,727,156 | B2* | 6/2010 | Angelsen ................ B06B 1/064 310/311 |
| 8,512,250 | B2* | 8/2013 | Quistgaard ................... 600/459 |
| 2003/0055337 | A1 | 3/2003 | Lin |
| 2003/0206940 | A1* | 11/2003 | Gott et al. .................... 424/443 |
| 2004/0010222 | A1* | 1/2004 | Nunomura et al. ............ 604/22 |
| 2004/0171980 | A1 | 9/2004 | Mitragotri et al. |
| 2004/0175347 | A1 | 9/2004 | Bissett |
| 2004/0267130 | A1* | 12/2004 | Angelsen ............ G01S 7/52022 600/458 |
| 2005/0043654 | A1 | 2/2005 | Matsumura et al. |
| 2008/0051680 | A1 | 2/2008 | Luebcke |
| 2011/0071482 | A1 | 3/2011 | Selevan |
| 2011/0178441 | A1 | 7/2011 | Tyler |

FOREIGN PATENT DOCUMENTS

| | | |
|---|---|---|
| CN | 1233968 | 11/1999 |
| EP | 0 679 371 A1 | 11/1995 |
| EP | 0 695 559 A2 | 2/1996 |
| EP | 1468708 | 10/2004 |
| FR | 2 844 715 A1 | 3/2004 |
| GB | 2303552 | 2/1997 |
| JP | 06-312023 | 11/1994 |
| WO | WO 91/12772 | 9/1991 |
| WO | WO 1998/07470 | 2/1998 |
| WO | WO 1998/25655 A2 | 6/1998 |
| WO | WO 99/34857 | 7/1999 |
| WO | WO 1999/39641 A1 | 8/1999 |
| WO | 99/48621 | 9/1999 |
| WO | WO 99/56829 | 11/1999 |
| WO | WO 99/62481 | 12/1999 |
| WO | WO 02/09729 | 2/2002 |
| WO | WO 2004/073769 A2 | 9/2004 |
| WO | WO 2004/078158 | 9/2004 |

OTHER PUBLICATIONS

2003 IEEE Ultrasonics Symposium Table of Contents.*
European Search Report dated Feb. 10, 2012, for related European application EP 11191016.2 (6 pgs).
International Search Report dated Mar. 13, 2006.
Watson et al, "Fabrillin-Rich Microfibrils are Reduced in Photoaged Skin. Distribution at the Dermal-Epidermal Junction", J. Invest Dermatol 112:782-787, 1999.
Watson et al, "A Short-Term Screening Protolcol, Using Fibrillin-1 as a Reporter Molecule, for Photoaging Repair Agents", J Invest Dermatol 116:672-678, 2001.
Brennan et al, "Matrix Metalloproteinase-1 is the Major Collagenolytic Enzyme Responsible for Collagen Damage in UV-irradiated Human Skin", Photochemistry and Photobiology, 2003, 78(1):43-48.
Watson et al, "Retinoic acid receptor a expression and cutaneous ageing", Mechanisms of Ageing and Development 125 (2004) 465-473.
Jantschitsch et al, "Heat shock and UV-B-induced DNA damage and mutagenesis in skin", Photochem. Photobiol. Sci., 2003, 2 899-903.
Debure et al, "Intracellular clusterin causes juxtanuclear aggregate formation and mitochondrial alteration", Journal of Cell Science 116, 3109-3121, 2003.
Trautinger et al, "Heat shock proteins in the photobiology of human skin", Journal of Photochemistry and Photobiology B: Biology 63 (2001) 707-77.
Maytin et al, "Hyperthermia Induces Resistance to Ultraviolet Light B in Primary and Immortalized Epidermal Keratinocytes", Cancer Research 53, 4952-4959, 1993.

Lage et al, "Non-coherent visible and infrared radiation increase survival to UV (254 nm) in *Escherichia coli* K12", J. Photochem. Photobiol. B: Biol., 54 (2000) 155-161.
Gutsmann-Conrad et al, "The Expression of Heat Shock Protein 70 Decreases with Cellular Senescence in Vitro and in Cells Derived from Young and Old Human Subjects", Experimental Cell Research 241, 404-413 (1998).
Verbeke et al, "Reduced Levels of Oxidized and Glycoxidized Proteins in Human Fibroblasts Exposed to Repeated Mild Heat Shock During Serial Passaging in vitro", Free Radical Biology & Medicine, vol. 31, No. 12, pp. 1593-1602, 2001.
Fonager et al, "Mild stress-induced stimulation of heat-shock protein synthesis and improved functional ability of human fibroblasts undergoing aging in vitro", Experimental Gerontology 37 (2002) 1223-1228.
Smith et al, "Spatial and Temporal Control of Transgene Expression Through Ultrasound-Mediated Induction of the Heat Shock Protein 70B Promoter In Vivo", Human Gene Therapy 13:697-706 (2002).
Barnett et al, "Current Status of Research on Biophysical Effects of Ultrasound", Ultrasound in Med. & Biol. vol. 20, No. 3, pp. 205-218, 1994.
Ruckman et al, "Alterations in stress protein synthesis and cardiac function of chick embryos exposed to heat shock or ultrasound", Toxicologist, 30, 198, 1996.
Ter Haar, G., "Tissue Regeneration", in 13 Ultrasound—Medical Applications, Biological Effects and Hazard Potential, Plenum Press, 1987.
Ter Haar, G., "Recent Advances and techniques in therapeutic ultrasound", in—Ultrasound—Medical Applications, Biological Effects and Hazard Potential, Plenum Press, 1987.
Mathew et al, "Heat Shock Response and Protein Degradation: Regulation of HSF2 by the Ubiquitin-Proteasome Pathway", Molecular and Cellular Biology, vol. 18, No. 9, pp. 5091-5098, 1998.
Babizhayev et al, "NMR spin-echo studies of hydration properties of the molecular chaperone α-crystallin in the bovine lens", Biochimica et Biophysica Acta 1598(1), pp. 46-54(9), 2002.
McClaren et al, "Dynamic Changes in Intracellular Localization and Isoforms of the 27-kD Stress Protein in Human Keratinocytes", J. Invest. Dermatol. 102:375-381, 1994.
Guesdon et al, "Interleukin 1 and Tumor Necrosis Factor Stimulate Two Novel Protein Kinases That Phosphorylate the Heat Shock Protein hsp27 and β-Casein", The Journal of Biological Chemistry, vol. 268, No. 6, pp. 4236-4243, 1993.
Jantschitsch et al, "Expression of the small heat shock protein HSP 27 in developing human skin", British Journal of Dermatology, 139:247-253, 1998.
Trautinger et al, "Human Keratinocytes In Vivo and In Vitro Constitutively Express The 72-kD Heat Shock Protein", J. Invest. Dermatol. 101:334-338, 1993.
Draper et al, "Rate of Temperature Increase in Human Muscle During 1 MHz and 3 MHz Continuous Ultrasound", Journal of Orthopaedic & Sports Physical Therapy, vol. 22, No. 1, pp. 142-150, 1997.
Mitragotri et al, "Determination of threshold energy dose for ultrasound-induced transdermal drug transport", Journal of Controlled Release 63, pp. 41-52, 2000.
Boucaud et al, "Effect of Sonication parameters on transdermal delivery of insulin to hairless rats", Journal of Controlled Release 81, pp. 113-119, 2002.
Zhang et al, "The Influence of Pulsed Low-Intensity Ultrasound on Matrix Production of Chondrocytes at Different Stages of Differentiation: An Explant Study", Ultrasound in Med. & Biol. vol. 28, Nos. 11/12, pp. 1547-1553, 2002.
Ziskin, Applications of Ultrasound in Medicine—in—Ultrasound, Medical Applications, Biological Effects and Hazard Potential, Repacholi et al, Plenum Press, 1987.
Hogan et al, "The Effect of Ultrasound on Microvascular Hemodynamics in Skeletal Muscle: Effects during Ischemia", Microvascular Research 23, 370-379, 1982.
Reher et al, "Therapeutic Ultrasound for Osteoradionecrosis: an In Vitro Comparison Between 1 MHz and 45 kHz Machines", European Journal of Cancer, vol. 34, No. 12, pp. 1962-1968, 1998.

(56) References Cited

OTHER PUBLICATIONS

Reher et al, "Effect of Ultrasound on the Production of IL-8, Basic FGF and VEGF", Cytokine, vol. 11, No. 6, pp. 416-423, 1999.

Li et al, "Cytokine release from osteoblasts in response to ultrasound stimulation", Biomaterials 24, pp. 2379-2385, 2003.

Goss et al, "Ultrasonic Absorption and Attenuation in Mammalian Tissues", Ultrasound in Med. & Biol., vol. 5, pp. 181-186, 1979.

Lehmann et al, "Selective Heating Effects of Ultrasound in Human Beings", Arch. Phys. Med. Rehab., 47, pp. 331-339, 1966.

Zietara et al, "Thermostability of Lactate Dehydrogenase $LDH-A_4$ Isoenzyme: Effect of Heat Shock Protein DnaK on the Enzyme Activity", Int. J. Biochem. Cell Biol. vol. 27, No. 11, pp. 1169-1174, 1995.

Julian et al, "Mechanism for Ultrasonically Enhanced Transmembrane Solute Permeation", Journal of Controlled Release, 12, pp. 77-85, 1990.

Watson et al, "Effect of Ultrasound on the delivery of photoageing repair agents", British Journal of Dermatology 155, pp. 245-246, 2006.

Miyazaki et al, "External Control of Drug Release and Penetration. VI[1]) Enhancing Effect of Ultrasound on the Transdermal Absorption of Indomethacin from an Ointment in Rats", Chem. Pharm. Bull. vol. 40, No. 10, pp. 2826-2830, 1992.

Rattan et al, "Hormetic Prevention of Molecular Damage during Cellular Aging of Human Skin Fibroblasts and Keratinocytes", Ann. N.Y. Acad. Sci. 1100:424-430, 2007.

Asano et al, "Effect of Pulsed Output Ultrasound on the Transdermal Absorption of Indomethacin from an Ointment in Rats", Biol. Pharm. Bull. 20(3), 288-291, 1997.

Tezel et al, "Incorporation of lipophilic pathways into the porous pathway model for describing skin permeabilization during low-frequency sonophoresis", Journal of Controlled Release 83, pp. 183-188, 2002.

Locke et al, "Enhanced postischemic myocardial recovery following exercise induction of HSP 72", Am. J. Physiol. 269 (Heart Circ. Physiol. 38): H320-H325, 1995.

Webster et al, "The role of ultrasound-induced cavitation in the 'in vitro' stimulation of collagen synthesis in human fibroblasts"; Ultrasonics, pp. 33-37, 1980.

Ogura et al, "Low-frequency sonophoresis: Current status and future prospects", Advanced Drug Delivery Review 60, pp. 1218-1223, 2008.

Weimann et al, "Transdermal Delivery of Poly-L-Lysine by Sonomacroporation", Ultrasound in Med. & Biol. vol. 28, No. 9, pp. 1173-1180, 2002.

Rattan, "Repeated Mild Heat Shock Delays Ageing in Cultured Human Skin Fibroblasts", Biochemistry and Molecular Biology International, vol. 45, No. 4, pp. 753-759, Jul. 1998.

Miyazaki et al, "External control of drug release and penetration: enhancement of the transdermal absorption of indomethacin by ultrasound irradiation", J. Pharm. Pharmacol. 1991, 43:115-116.

Tezel et al, "A Theoretical Analysis of Low-Frequency Sonophoresis: Dependence of Transdermal Transport Pathways on Frequency and Energy Density", Pharmaceutical Research, vol. 19, No. 12, pp. 1841-1846, Dec. 2002.

Harvey et al, "The 'in vitro' stimulation of protein synthesis in human fibroblasts by therapeutic levels of ultrasound", Proc $2^{nd}$ Eur Congress on Ultrasonics in Medicine, Munich, 1975.

S.R.A. Development Ltd.—Duo Son "Technical Specs" retrieved Jul. 20, 2010 from http://dialspace.dial.pipex.com/town/lane/xib90/duoson.htm (2 pages) "© 2003".

501(k) Summary; Orthosonics Due-Son; Ultrasound Diathermy Device; Orthosonics, Ltd. Jun. 16, 1997 (5 pages).

\* cited by examiner

APPARATUS FOR TREATMENT OF DERMATOLOGICAL CONDITIONS

This application is a divisional of application Ser. No. 11/664,098, which was filed on Mar. 29, 2007 now abandoned (published as US 2008-0051680-A1 on Feb. 28, 2008), which is a U.S. national phase of International Application No. PCT/GB2005/050181 filed 11 Oct. 2005 which designated the U.S. and claims priority to GB 0422525.6 filed 11 Oct. 2004, the entire contents of each of which are hereby incorporated by reference.

TECHNICAL FIELD

This invention relates to ultrasound delivery apparatus, methods and topical compositions for the treatment of skin, in particular for the treatment of cosmetic skin conditions and to improve the appearance of sun damaged and/or aged skin; the invention further relates to the use of such apparatus and compositions in methods of treating skin, which methods may incorporate the application of ultrasound.

BACKGROUND TO THE INVENTION

The skin is a potential route for delivery of pharmaceutical or cosmetically active agents to the body. However, the skin is not generally thought of as an efficient delivery route, due to the low permeability of the stratum corneum and the epidermis in general. Traditionally, topical application of pharmaceutical therapeutic agents has been targeted at localized dermatological sites. More recently, transdermal techniques have been used for systemic targeting especially as this route bypasses the hepatic circulation where degradation of the active agent may occur.

Ultrasound can be used to deliver molecules to within the skin. When ultrasound is used in this context it is termed "sonophoresis". Ultrasound applied to the skin has two main effects. First, cavitation results from the rapidly oscillating pressure field, causing bubble formation and collapse, which mechanically creates channels through the stratum corneum. The second effect is the direct heating of the material through which the sound waves are travelling, due to attenuation of the acoustic energy through reflection, absorption and dispersion. In skin, this occurs up to four times more than other tissues due to its heterogeneity. Heating is known to disrupt the lipid bilayer system in the stratum corneum also contributing to the enhanced permeability of the epidermis. Several factors can affect the heating capacity of ultrasound, including:
(i) applying ultrasound in continuous rather than pulsed mode,
(ii) prolonging the exposure time,
(iii) focusing the ultrasound rather than using unfocused application,
(iv) avoidance of using aqueous gels which are used to decrease the degree of reflection,
(v) applying the ultrasound at higher power densities,
(vi) application of ultrasound to tissues immediately adjacent to bone.

With ultrasound, diffusion of low molecular weight molecules has been shown to increase by 2-5000 times across isolated epidermis in vitro and by up to 1700 times in theoretical studies. Even large molecule drugs such as insulin and heparin have been delivered effectively when using 15 minutes of 20 kHz US. One in vitro study found that poly-L-lysine molecules of up to 51 kDa could be delivered with ultrasound at 20 kHz and intensities in the range of 2 to 50 $W/cm^2$. By way of explaining this increase in permeation, some studies have reported an increase in the number of pores rather than an increase in the individual pore diameters (28±12 Å). However, the term 'sonomacroporation' has been adopted for specific ultrasound that actually causes larger pore formation.

The permeability of the skin is increased by disruption of the intercellular lipids through heating and/or mechanical stress, and through the increase in porosity. Temperature rises of 6° C. (1 MHz, 0.25 $W/cm^2$) to 50° C. (20 kHz, 10-30 $W/cm^2$) have been reported, but rises as little as 11° C. (1 MHz, 2 $W/cm^2$) have been shown to cause skin damage. Continuous mode ultrasound at an intensity of 1 $W/cm^2$ raises the temperature of tissue at a depth of 3 cm to 40° C. in 10 minutes. For smaller molecules, such as mannitol, enhancement of permeation through the skin occurs when ultrasound is applied as a pre-treatment or simultaneously with application of the molecule; whereas for large molecules such as insulin, enhancement of permeation has only been recorded during application of ultrasound.

Ultrasound can be used to improve transdermal drug delivery. WO 99/34857 discloses transdermal drug delivery of various active agents using a power density of less than 20 $W/cm^2$, preferably less than 10 $W/cm^2$; the frequency used being less than 2.5 MHz, preferably less than 2 MHz, preferably less than 1 MHz, most preferably 20-100 kHz; Experimental data in vivo on rats was generated using a frequency of 20 kHz and a power density of 1 or 1.5 or 7 $W/cm^2$.

U.S. Pat. No. 4,767,402, describes transdermal drug delivery using ultrasound at a power density of 0-3 $W/cm^2$, preferably 0.5-1.5 MHz, and recommends that as the power density is reduced, the frequency should also be reduced. A power density of 1-2 $W/cm^2$ at frequency 870 kHz is exemplified.

Cosmetic treatments that aim to improve skin quality are also hindered by the barrier function of the epidermis and in particular the outer stratum corneum. The epidermis provides a significant mechanical and chemical barrier to solute transfer due to the cornified cell/lipid bilayer. Also, there is significant enzymatic activity in the epidermis and dermis, which provides a biochemical defence to neutralise applied xenobiotics and which is comparable to that of the liver in terms of activity per unit volume. Additionally, the molecular weight of active substances is known to be important in determining their propensity to diffuse across the skin. Diffusion of substances of molecular weight around 500 Da and above is known to be inefficient. Methods and apparatus involving ultrasound have been described for use in cosmetic of the skin and in medical treatments.

U.S. Pat. No. 6,113,559 discloses a method and apparatus of reducing wrinkles by application of a focused ultrasound beam (ultrasound power density 100-500 $W/cm^2$, frequency 1-500 MHz) to a region of skin, so that the energy delivered to the dermis layer is sufficient to heat the tissue in order to stimulate or irritate the dermis layer, causing a change in the dermis layer that confers a change in smoothness of the epidermis layer.

Ultrasound therapy for the treatment of cellulite is well known and the application of ultrasonic wave energy has generally proven effective in breaking down subcutaneous fatty tissue. As an example, EP 0 695 559, relates to multifunctional equipment for treatments of cellulite, which can include emitters of ultrasonic vibrations for application to, for example, the thighs of a patient's body. However, suitable power densities and frequencies are not discussed. GB 2303552 discloses ultrasound apparatus useful for the non-invasive reduction of cellulite. The ultrasound devices are used for the ultrasonic treatment of cellulite at a predetermined frequency of about 3.3 MHz and a typical power density of 2.8 W/cm$^2$, with 50% of the energy being absorbed within a depth of from 1.27 cm to 2.54 cm below the skin surface.

U.S. Pat. No. 6,030,374 discloses a method for enhancing transport of an active agent through the skin by exposing skin to ultrasound and applying an active agent to the skin by injection. The active agent may be used to reduce the appearance of cellulite. For lower frequency ultrasound, an ultrasound frequency between 25 kHz and 3 MHz at a power density of 0.5-2.0 W/cm$^2$ is used; for higher frequency ultrasound, an ultrasound frequency between 3 MHz and 16 MHz at a power density of 0.2-1.0 W/cm$^2$ is used.

U.S. Pat. No. 5,665,053 relates to an endermology body massager having ultrasound generators that are selectively controlled by the operator. The very low frequency long wave ultrasound disclosed, 10 to 40 kHz, is in the range generally recognised as being disruptive ultrasound, which may be damaging to cells, and thus for safety reasons this is not suitable for general use except at very low power levels.

U.S. Pat. No. 5,507,790 discloses apparatus for focusing ultrasound energy such that the temperature of a site within the patient's subcutaneous adipose tissue layer is raised to between 40.0 and 41.5° C., to accelerate local fat tissue lipolysis reaction rates. The apparatus includes an ultrasonic transducer which supplies ultrasound energy of an undisclosed frequency and at an undisclosed power density to a focusing element.

WO 99/56829 discloses ultrasound bandages and ultrasound transducer array bandages which are said to be useful to accelerate the healing of wounds by positioning the ultrasound bandages and ultrasound transducer array bandages adjacent to a wound and generating ultrasonic pulses.

WO 99/48621 describes large-area flexible piezoelectric composite transducer elements and large-area arrays of such transducer elements have sufficient flexibility to conform to the contours of the human anatomy, e.g., the hip, spine.

To be effective, treatment for cosmetic skin conditions, such as skin ageing and sun damage, must deliver actives to at least the depth of the upper (papillary) dermis and therefore must employ a mechanism to overcome this effective physical and biochemical barrier, even when it has deteriorated with age.

The deterioration of human skin due to natural or 'intrinsic' ageing is characterised by a number of symptoms. Such symptoms include a thinning of both the epidermis and the dermis, a flattening of the junction between them, poor wound healing, thermoregulation and immune function along with a deterioration of associated mechanical properties such as tear resistance, elasticity and barrier function. The visible appearance also deteriorates giving a rougher, lined and dry appearance along with uneven pigmentation. In most cases skin ageing is of little medical importance except in such cases as impaired wound healing which allows infection and dysfunction.

Visible deterioration in skin with age is due to a combination of several changes which happen more or less concurrently. This deterioration can be accelerated by lifestyle choices such as smoking and sunbathing. The visibly apparent changes include: sagging skin, rough skin texture, dyspigmentation, dull complexion and a general loss of radiance. Wrinkling, or rhytide formation, is probably the symptom most commonly associated with skin ageing and is known to be caused by a change in the type and distribution of matrix proteins and proteoglycans. Similarly, functions of the skin that decline with age include: cell replacement, immune recognition, sensory perception, injury response, vascular responsiveness, vitamin D production, barrier function, thermoregulation, sebum production, chemical clearance, sweat production and mechanical protection. There may also be changes in pH (from 4.5 to 5).

Ageing skin is characterised by decreased epidermal thickness and proliferation along with the flattening of the rete ridge pattern. The apparent thinning may be linked to increased apoptosis in the basal and spinous layers, in conjunction with impaired cell proliferation of the basal layer. Senescent skin thins, becomes less elastic and has reduced barrier function. This is because the dermis contains a reduced cellular content with stiff, inflexible matrix proteins and a diminished number of capillary loops. The overlying epidermis consequently suffers because the dermal-epidermal junction (DEJ) flattens, resulting in a reduced contact surface area as there are fewer capillary loops in proximity to the DEJ. The exchange of nutrients and metabolites between the two layers decreases and the communication needed to maintain layer integrity in response to changes in external environment conditions is impaired.

The skin is not only subjected to intrinsic or chronological ageing processes, but also environmental or extrinsic ones. For example, factors such as diet, pollution and smoking are known to affect the rate of skin ageing. However one factor stands out as the most potent 'gerontogen': sunlight. It has been suggested that approximately 80% of facial ageing is due to sun exposure.

Collagen, elastin and other intra- and extracellular proteins of the skin are affected resulting in solar elastosis, the build-up of localised elastic tissue in fibrous bundles throughout the dermis.

The UV component of sunlight has also been linked to the reduction in cellular population of the epidermis (keratinocytes) and dermis (fibroblasts). It has been suggested that this is due to the increase in programmed cell death or apoptosis. The epidermis and the dermis are known to become increasingly acellular with age, which supports this hypothesis. Despite the epidermis influencing the dry and rough appearance of the skin, it is the dermis that dictates the degree of surface smoothness. Reduction and/or a redistribution of matrix proteins and high water-binding proteoglycans largely govern the appearance of wrinkles and general surface smoothness. Similarly, scarring of the skin is due to abnormal protein content, conformation and distribution via the formation of granulation tissue following trauma, again primarily a dermal rather than an epidermal problem.

Typical symptoms of photoageing include coarseness, wrinkling, irregular pigmentation, telangiectasia, scaliness and a variety of benign, premalignant and malignant neoplasms. Photoageing is predominant in fair-skinned Caucasians who have a history of sun-exposure and occurs most severely on the face, neck and extensor surfaces of the upper extremities. Elastosis, recognised as the pebbly goose flesh seen on the neck and upper chest, is due to nodular aggregations of altered elastin fibres in the dermis. A proliferation of increasingly thickened and tangled elastin fibres has been observed in the papillary and reticular dermis of sun-exposed skin. Even in mildly sun-damaged skin, a 5-20 fold increase in elastin fibre diameter has been found, with slight changes in the fibrillar structure and an alteration of the normal architecture, giving a disrupted and "moth-eaten" appearance.

Overall, photodamage is manifested by the progressive injury to dermal fibroblasts with quantitative and qualitative alterations to the supporting extracellular matrix. As solar energy passes through the skin and is absorbed a gradient of damage occurs, the most damage being seen in the outer papillary dermis, with less to the deeper reticular dermis.

Intrinsic (chronological) aging is characterised by atrophy of skin with loss of elasticity and reduced metabolic activity. Specifically, the stratum corneum remains unchanged, but the epidermis thins overall, with a flattening of the dermal-epidermal junction resulting in increased fragility of the skin. Dermal thickness and dermal vascularity are decreased; this is accompanied by a decrease in the number and the biosynthetic activity of dermal fibroblasts. This latter change is manifested by delayed wound healing. Increasing age also has the effect of reducing the response of keratinocytes and fibroblasts to growth factors.

At the molecular and ultrastructural level, there are changes in elasticity and other changes in matrix proteins. As regards elasticity, there is a reduction in the extracellular protein fibrillin which is a major component of microfibril bundles that connect the dermal-epidermal junction to the papillary dermis. These bundles, often called oxytalan fibres, essentially provide an elastic connection between the epidermis and dermis. Previously considered to be synthesised only by fibroblasts, the fibres present at the dermal-epidermal junction have been shown to be synthesised by keratinocytes. The concentration of fibrillin in photoaged skin has been found to be decreased and has proved to be a useful biomarker for photoageing as it is known to be connected with wrinkle formation. Fibrillin concentration is also reduced in skin that has been subjected to tensile stress and exhibits stretch marks (striae distensae).

In vivo proteins are post-translationally modified by a non-enzymatic reaction (Maillard reaction) between proteins (both intra- and extracellularly) and sugars. This reaction is known either as glycation, or glycosylation, and is well recognized to play an important part in protein turnover, tissue remodelling, diabetes and ageing. In skin, this process is exacerbated by UV, with dermal glycation often increasing significantly after 35 years. Glycation of proteins occurs when reducing sugars such as glucose and fructose, or their reactive intermediates such as glyoxal, react with the amino groups of long half-life proteins such as collagen ($t_{1/2}$=15 years in human skin) and elastin in the dermis. As a result of this process, cytotoxic Advanced Glycation End-products (AGEs) (AGEs) accumulate.

An increase in glycation has been seen in skin previously irradiated with UV. A well-known biomarker for protein glycation, carboxymethyllysine (CML), has been shown to be present predominantly in areas of solar elastosis in the dermis and generally at higher concentrations in photoaged skin, suggesting that UV-induced oxidation may accelerate the formation AGEs in photoaged skin.

The build-up of AGEs has several effects. Advanced glycation end product-modified proteins are endogenous sensitizers of photo-oxidative cell damage in human skin by UVA-induced generation of reactive oxygen species (ROS) contributing to photoageing and photocarcinogenesis. ROS generation has also been linked to early and late stages of AGE formation with a direct link with the rate of ROS generation which in turn increases matrix metalloproteinase expression with a consequent decrease in healthy digestible matrix. There is also cross-linking of extra-cellular proteins which causes deterioration of the structural mechanical properties of the protein and reduces their susceptibility to the body's natural enzymes, such as matrix metalloproteinases (MMPs), which normally ensure a regular, healthy protein turnover. Cross-linking AGEs include species such as pentosidine. Non-cross-linking AGEs include species such as CML. Glycation also decreases water accessibility of proteins making them more heat stable and less likely to be thermally denatured.

The body has a host of physiological mechanisms that defend against deleterious protein modifications, including protein-digesting enzymes. Timely proteolysis removes damaged proteins before they undergo oxidative damage and cross-linking. Therefore, rapid effective proteolysis is essentially an anti-aging mechanism. It has been mentioned already that proteins such as collagen and elastin, which have been post-translationally modified through UV-induced glycation, are more resistant to digestion by endogenous enzymes (e.g. metalloproteinases). This, coupled with the increase in expression of such enzymes, further reduces the ratio of healthy digestible matrix proteins to modified deleterious proteins.

Not only are native proteins turned over by endogenous enzymes such as collagenase and elastase, but other systems are present both intra- and extracellularly to deal with ageing and/or denatured/stressed proteins. One such mechanism employs molecular chaperones. Increasing age is associated with a reduced capacity to maintain homeostasis in all physiological systems and this may result, in part at least, from a parallel and progressive decline in the ability to produce heat shock proteins. An attenuated heat shock protein response may contribute to increased susceptibility to environmental challenges in aged individuals.

Heat Shock Proteins (HSPs), also known as stress proteins, are thought to act as molecular chaperones by assisting with protein synthesis, transport, folding and degradation. They are a group of proteins that are present in all cells, in all life forms. They are induced when a cell undergoes environmental stress, heat, cold, or oxygen deprivation. HSPs are also present in cells under perfectly normal conditions and have been linked to modulation of contraction and relaxation responses in vascular smooth muscle; they play an important role in protein folding and function, even in the absence of stress.

The formation of Advanced Glycation End-products causes protein unfolding irreversible cross-linking and other chemical modifications. HSPs are known to promote refolding/maintenance of conformation and also the rapid degradation of irreversibly-damaged proteins. Small heat shock proteins, such as α-crystallin, are known to protect eye lens proteins from glycation induced changes. Small heat shock proteins (sHSPs) are known to have common 'crystallin' core that appears to be responsible for the catalytic activity of these chaperones. It has been suggested that a greater understanding of α-crystallin/sHsp chaperone action will have implications for the development of therapeutics to treat and prevent cataract.

The heat shock protein family includes the 8-kD ubiquitin (known in connection with the ubiquitin-proteasome protein degradation pathway), 32-kD heme oxygenase-1 (connected to UVA induced oxidative stress) and HSP-47, a known collagen chaperone. HSP-27 has been found in human skin and has been suggested to play a protective role in inflammatory diseases due to its links with interleukin-1 and tumour necrosis factor-α. This, along with the understanding that HSP-27 expression is closely linked with epidermal keratinocyte differentiation suggests that heat shock proteins such as HSP-27 play a role in skin protection and possibly in the UV-sunburn inflammation cycle. In contrast to other cells and organ systems, epidermal keratinocytes are known to express HSP-72 constitutively, i.e. without exposure to previous stress. The heat shock protein HSP47 has been shown to be important as a molecular chaperone for procollagen synthesis in human fibroblasts. HSP47 synthesis is reduced in aged and photo-aged skin.

HSP expression following exposure to UV has been linked with increased resistance to UV-induced cell death. Non-toxic inducers of HSPs may protect against the immediate and long-term effects of UV exposure. Studies have shown that prior exposure of cells to red and infra-red (IR) light protects them against subsequent exposure to UV light. Similarly, IR pre-treatment of cells also protects cells against subsequent lethal (51° C.) applied heat stress.

The well-known protective effect of HSPs from environmental stress is not constant with age. The HSP response to stress is attenuated with age, probably at the transcriptional level. Repetitive mild heat shock (RMHS) of human skin fibroblasts has been found to reduce the rate of age-related changes. One study has connected the age-related decrease in the ability of human fibroblasts to reduce the accumulation of glycated proteins with a parallel reduction in the ability to express HSP70, as human fibroblasts exposed to RMHS exhibited increased HSP70 expression and reduced accumulation of glycated protein accumulation. The beneficial effects of RMHS have been attributed to increased proteasomal activity, increased ability to decompose $H_2O_2$, reduced accumulation of lipofuscin and an enhanced resistance to UVA radiation.

Temperature rises of 3-5° C. above baseline in muscle have been shown to cause the induction of HSPs. Induction of HSPs by 30 mins of pulsed ultrasound applied at normal body temperature has been demonstrated in the rat embryo, showing that the heat shock response is not specific to heat but can occur in response to mechanical stress. Similarly, chick embryos exposed to ultrasound, without any significant thermal contribution, have shown heightened synthesis of HSP72 suggesting that the mechanical stimulus can induce a stress response. It was also concluded that to produce a 'full biological effect, stress must be constant for approximately 10 s or more over any time interval during exposure'. It is possible that cumulative effects can stimulate HSP production as has been found when mild heat shock was repeated over 3 days causing significantly elevated muscle HSP levels.

Certain substances have an effect on HSP expression. For example, salicin has been shown to reduce the necessary degree of temperature rise from 42° C. to 39° C. to elicit HSP expression and to reduce the degree of subsequent UV-induced damage in cultured human fibroblasts and keratinocytes. Known irritants such sodium lauryl sulphate (SLS) also induce HSP expression. HSP27 upregulation due to SLS application to excised human skin has been used as a method of determining cellular stress due to chemical irritancy. In a similar study, however, SLS induced expression of HSP27 in human epidermis was suppressed by topical application of vitamin C.

The substance zinc-L-carnosine, known also as Polaprezinc commercially, has been shown to induce HSP72 (stress-induced HSP70) expression in gastric mucosa protecting cells from applied stress through chemical irritancy. As a control, $ZnSO_4$ and carnosine were also tested and found not to elicit the same response. Known as an anti-ulcer drug, zinc-L-carnosine's wound-healing action has been linked to its proliferative response in non-endothelial cells such as fibroblasts.

The influence of aspirin on HSP70 expression in intact rats subjected to heat stress has been investigated. Rats were injected intraperitoneally either with aspirin (100 mg/kg), or vehicle alone, 60 min prior to their placement at 37° C. or room temperature for 30 min. The combination of aspirin with heat treatment resulted in 3 to 4 fold higher levels of HSP70 mRNA relative to those seen with heat treatment alone.

The role of HSP-72 and -70 in conferring resistance to aspirin attack of the rat gastric mucosa has been investigated; expression of these HSPs was elevated following chronic exposure to aspirin.

Analgesics such as aspirin, ibuprofen and paracetamol are known to protect against cataract. This action has been attributed to the inhibition of sugar-induced cross-linking in small HSPs such as α-crystallin. Enzymes that protect against cataract are prone to glycation-induced inactivation, but aspirin has been shown to protect against this.

Similarly, acetyl-L-carnitine has been recognised as a potential chaperone-protecting agent due to its abilities to acetylate potential glycation sites of small HSPs and correspondingly protect them from glycation-mediated protein damage.

Small heat shock proteins (sHSPs) and Clusterin are molecular chaperones that share many functional similarities despite their lack of significant sequence similarity. Small heat shock proteins are ubiquitous intracellular proteins whereas clusterin is generally found extracellularly. Both chaperones prevent the amorphous aggregation and precipitation of target proteins under stress conditions such as elevated temperature, reduction and oxidation. Transcription of both HSPs and clusterin are mediated by the transcription factor HSF-1. However, clusterin has been shown to be much more efficient than certain sHSPs, such as α-crystallin, in preventing the precipitation from solution of stressed target proteins.

Clusterin is expressed as a 75-80 kDa heterodimeric protein that is heavily glycated such that 30% of its mass is comprised of sugar. Whereas the chaperone activity of small heat shock proteins such as α-crystallin is reduced significantly at lower pH, the activity of clusterin is enhanced at lower pH. This has important implications for sites of tissue damage or inflammation where local acidosis (pH<6) occurs. Another similarity that clusterin shares with sHSPs is the ability to regulate apoptosis. Over-expression of clusterin can protect cells from a variety of agents (e.g. TNF-α and UV irradiation) that otherwise induce apoptosis. It has been suggested that clusterin may interact with stressed cell surface proteins to inhibit pro-apoptotic signal transduction or prevent inappropriate interactions of intracellular proteins during stress.

Many topical skin preparations are available for the treatment of medical skin conditions and for the treatment of cosmetic skin conditions, in particular skin ageing and sun damage. In many instances these preparations are ineffective, with only minimal or short lived efficacy. There is thus a desire for new preparations effective in the treatment of skin conditions. Furthermore, the present invention addresses the problems of achieving efficient delivery to the skin of such novel preparations.

DISCLOSURE OF INVENTION

The invention provides an apparatus for application of ultrasound to the skin comprising a plurality of ultrasound transducer elements arranged as an array in a flexible material in spaced configuration, wherein the ultrasound transducer elements are capable of delivering ultrasound at low and/or high frequency to an area of the skin.

According to this aspect of the invention, an ultrasound array can be incorporated into a mask, patch or patches that can be applied to the skin to supply ultrasound.

The mask or patch is preferably shaped to conform to at least part of the surface of the face. Thus the flexible array of ultrasound transducer elements can be formed in a circular or any other simple or complex shape, especially those optimised to conform to bodily shapes and features, especially the parts of the face and neck. The array should be sufficiently flexible to allow bending to a curvature of 3-4 cm radius, preferably to allow bending to shape around doubly curved surfaces as well as singly curved surfaces.

Application of ultrasound using an apparatus according to the invention can be used as a pre-treatment before application of a composition of the invention, or a composition of the invention can be applied to the skin, either directly or via material impregnated with the composition, e.g. a pad, such as a gel pad, and then the ultrasound delivered via the flexible array. The flexible ultrasound array can be coupled to a thin (2-3 mm), disposable gel pad that contains the composition and couples the ultrasound energy. Suitably the flexible array can be affixed, directly or indirectly (e.g. via a pad) to the skin for the duration of the treatment.

The transducer elements of the array are preferably hermetically sealed, e.g. contained within a waterproof flexible material capable of electrical performance even when adhered/coupled to aqueous formulations.

In the apparatus, it is preferred that the flexible material is at least approximately acoustically matched, to one or preferably both of the transducer elements, to inhibit generation of reflections in the material that might divert or otherwise dissipate the ultrasound waves. The flexible material may comprise a polymeric material selected from thermoplastics, thermosets, rubbers or mixtures thereof. The flexible acoustically matched material will ordinarily be formed from a polymeric material, and optionally, a filler. The polymeric material should have good compatibility with the components of the transducer element, biocompatibility and flexibility. Suitable polymeric materials include thermoplastics such as high density polyethylenes, polymethyl methacrylates, polypropylenes, polybutylene terephthalates, polycarbonates, polyurethanes such as CA 118 and CA 128 available from Morton Chemical and estane polyester, and the like; thermosets such as epoxies such as Spurr epoxy and Stycast 80, Stycast 1365-65 and the like; and rubbers such as silicone rubbers such as dispersion 236 available from Dow Corning and RTV-141 available from Rhone-Poulenc, Inc. and the like. If desired, the acoustic impedance of the polymeric materials may be increased by the incorporation of one or more fillers. Suitable fillers include PZT, tungsten, alumina, silica glass, tungsten carbide, titanium, glass powder and the like with glass powder being preferred. The size of the filler particles should be in the range of about 0.1 to about 50 microns and preferably from about 0.5 to about 5 microns. The amount of filler employed will be that amount necessary to impart the desired acoustic impedance. Normally, from about 2 to about 50 percent filler by volume and preferably from about 5 to about 30 volume percent filler is employed. A preferred polymeric material is silicone rubber.

Typically the transducer elements will be individually connected to a ultrasound generator, such that the ultrasound transducer elements are capable of delivering low and high frequency ultrasound simultaneously or sequentially.

An apparatus according to the invention can comprise a flexible array having a set of high frequency transducer elements and a set of low frequency transducer elements respectively capable of delivering high and low frequency ultrasound. The high and low frequency transducers may be alternated, or otherwise arranged in a pattern, for example a substantially regular arrangement of the two types of transducers. In other embodiments the high and low frequency elements may be mounted together, e.g. on top of one another, in particular coaxially. In this aspect the transducer elements may be dual frequency transducer elements capable of delivering low and high frequency ultrasound sequentially or simultaneously, along a single axis. Dual frequency transducers may be arranged in a pattern, for example a substantially regular arrangement of dual frequency transducers. The transducers may be of circular or other regular or irregular shape. Transducers elements suitably comprise transducer materials known in the art, e.g. piezoceramics, PVDF, and/or piezoelectric materials such as PZT powders commercially available from Morgan Matroc, Inc., ceramic, single crystal relaxor ferroelectric, lead zirconate titanate Pb (Zr, Ti)O3, lead metaniobate Pb (Nb206), modified lead titanate PbTi3 such as (Pb, Ca)TiO3 and (Pb, Sm)TiO3, barium titanateBaTiO3, PMN-PT(1-x) Pb(Mg"3Nb2/3)O3-xPbTiO3, PZN-PT/BTNb2/3)O3-x(yPb-TiO3-(1-y)PbZrO3)Pb(Zn1/3Nb2/3)O3-xPbTiO3-BaTiO3, (1-x)Pb(Zn1/3, and the like.

In an apparatus according to the invention, transducer elements can be capable of delivering the low frequency component in pulsed mode and the high frequency component in continuous mode, or more preferably capable of delivering the low frequency ultrasound component in continuous mode and the high frequency ultrasound component in pulsed mode. The pulsed mode can be controllable, such that it is variable, to provide variable pulsing regimes, for example 2 ms on, 8 ms off (20% duty cycle).

In an apparatus according to the invention, suitably the transducer elements are capable of delivering a low ultrasound frequency of from 20 to 500 kHz, preferably ~50 kHz and/or a high ultrasound frequency of from 0.5 to 3.5 MHz, preferably ~1 MHz up to 3 MHz. The spatial average power density of the low frequency ultrasound energy is suitably from 20 to 500 mW/cm$^2$. The spatial average power density of the high frequency ultrasound energy is suitably from 0.5 to 3 W/cm$^2$.

In a second aspect, the invention provides a dual frequency transducer element comprising a high frequency transducer element and a low frequency transducer element, preferably the high and low frequency transducer elements are co-axially mounted and may be mechanically and electrically connected. In a preferred embodiment the high frequency transducer element comprises a piezo ceramic material and the low frequency transducer element comprises PVDF. The high and low frequency transducer elements can be bonded together, optionally with a spacer element in between, which may be a metal spacer element.

An apparatus according to the invention may comprise an array of dual frequency transducer elements as described herein.

The ultrasound array can be programmed to deliver a desired sequence of high and/or low ultrasound frequencies, in pulsed or continuous mode, in set patterns, thereby avoiding problems of over or under exposure of the skin the ultrasound, which can cause over-heating of the skin. An apparatus of the invention is controllable such that low and high frequencies are capable of being driven so that the ultrasound field moves across the array in a preset pattern and at a preset speed, for example 2-3 seconds from left to right across the full width (e.g. 5-10 cm) of the array then 2-3 seconds back again, i.e. 4-6 seconds cycle time; or into the centre of the array and then out again, especially if the array has circular shaped geometry. The pattern can be varied within the same treatment session, e.g. left to right then up and down. Ideally the high and low frequencies are applied so that each frequency covers the area being treated as evenly as possible. The flexible array is preferably configured such that ultrasound is not applied to the eye and such that the transducers will be sited and controlled so that the possibility of over exposure of skin which is in proximity to bone to ultrasound (e.g. cheek bones or the orbit of the eye) is minimised. This can be achieved by application of ultrasound in pulsed mode and for example by a delivering ultrasound in a pre-determined phased array sequence. Use of a mask, patch or patches to apply ultrasound is particularly suitable for home use.

The apparatus may comprise a power and control unit, which is suitably of an appropriate size to enable it to be held in the hand. The unit is preferably provided in a waterproof/wipe-clean casing. Power may be supplied from batteries, e.g. rechargeable batteries, to allow use away from mains supply. The unit is preferably provided with controls to allow the user to select settings for a desired treatment, these may include pre-set levels to enable the user to select settings for different uses, e.g. for anti-ageing treatments, cellulite treatment or for scar reduction, the various settings being based on different frequency and amplitude/power settings. Suitably the control unit may include a maximum time cut-out to prevent over-exposure, e.g. 10 minutes. A memory function may be provided, e.g. to record date and/or duration of treatment In a particularly preferred embodiment the invention relates to an ultrasonic treatment system comprising a plurality of transducer elements (15) arranged as an array (2) and held in proximity to each other by compliant material (4), which is suitably silicone rubber (FIGS. 1a, b and c).

Each element (15) may comprise two components, a high frequency transducer element, e.g. a piezo ceramic disc element (5) and a low frequency transducer element, e.g. a pvdf element (7) positioned so that the positive polarised electrode of each element is mechanically and electrically connected at interface (9). The upper surface (30) of the PZT element (5) and the lower surface (31) of the pvdf element (7) are connected together electrically (FIG. 1(d)). Each element (1) is individually connected to a power source described in FIG. 3 via spring connectors (8) attached to juxta-positioned contacts (3) on flexibly mounted plate (6) FIG. 1a. The transducer array may then be connected to an ultrasound generator via connectors (11).

FIGS. 2a and 2b show a particular form of the transducer element in which PZT disc (12) is conductively attached to metal element (13) which in turn is conductively attached to a pvdf material (24) via metal ring (23) and insulating spacer ring (22). The common HT connection (9) is achieved via conductive ring (21). Alternate drive frequencies of 50 kHz and 1 MHz are generated either by individual circuits in system FIG. 3B or via DDS chip in FIG. 3A. The combined transducer is thus alternatively energised in burst of 50 kHz and 1 MHz sine wave pulses. The length and ratio of activation signals may be processor controlled or derived from a sensor control related to measured characteristics of the target tissue.

In FIG. 2a, element (13) may be formed as a focussing device by shaping the lower surface with a shaped, focussing profile, e.g. a concave profile, thus imparting similar properties to the geometrically compliant pvdf film.

In a third aspect, the present invention provides a composition comprising one or more anti-glycation agent, one or more anti-oxidants, a dermatologically acceptable excipient or excipients and optionally one or more substance capable of inducing expression of a molecular chaperone.

Compositions of the invention are useful in the treatment of cosmetic skin conditions, in particular acting to improve the appearance of ageing skin, especially by ameliorating the effects of sun damage. Usually, the or each anti-glycation agent is present at from about 0.5 to 5%, preferably from about 1 to 3% w/w of the composition.

Suitably, in some embodiments of compositions of the invention, the anti-glycation agent(s) also has anti-oxidant activity.

Preferred anti-glycation agents for incorporation into compositions include one or more of a histidine containing dipeptide, alanyl-L-histidine (L-carnosine) or a peptidomimetic thereof, N-acetylcysteine, aminoguanidine, d-penicillamine, acetylsalicyclic acid (aspirin), paracetamol, indomethacin and ibuprofen and/or a functional homolog, derivative or prodrug thereof.

Histidine-containing natural dipeptides, such as L-carnosine (β-alanyl-L-histidine, or "carnosine") are known to be effective against different oxygen-derived free radicals, and also lipoperoxyl radicals. Carnosine, present at high concentrations in skeletal muscle tissue, can delay senescence and provoke cellular rejuvenation in cultured human fibroblasts. The mechanism by which such a simple molecule induces these effects is not known despite carnosine's well documented anti-oxidant and oxygen free-radical scavenging activities. In addition to the prophylactic actions of carnosine, it may also directly participate in the inactivation/disposal of aged proteins possibly by direct reaction with the carbonyl groups on proteins. The possible fates of these carnosinylated proteins include the formation of inert lipofuscin, proteolysis via the proteasome system and exocytosis following interaction with receptors.

It is believed that carnosine may tag glycated proteins for removal. Protein turnover relies on hydration for thermal denaturation and glycated proteins are known to have higher enthalpies of denaturation obviously rendering them less degradable. 'Carnosinylation' of glycated proteins, it has been suggested, may increase the water accessible surface of such proteins and therefore promote hydration and unfolding during thermal denaturation. This theory has been borne out by observing lower $\Delta H$ and $\Delta G$ denaturation for carnosinylated glycated proteins.

Carnosine acts as an anti-glycation agent, it inhibits carbonyl attack by methylglyoxal (MG) and by the AGE carboxymethyl lysine (CML). Carnosine itself has been shown to be readily glycated by a variety of sugars forming non-mutagenic adducts and its protective role has been attributed to effect of preventing glycation of crystallin, superoxide dismutase (SOD) and catalase. Carnosine has been found to offer a superior efficacy and toxicity profile when compared to the anti-glycation agent aminoguanidine, thus carnosine is a preferred anti-glycation agent.

Carnosine exhibits $Mn^+$ chelation and ROS scavenging properties, but these alone cannot adequately explain the effect it has in rejuvenating senescent fibroblasts. One study has attributed its properties to the reaction of carnosine with carbonyl groups on glycated/oxidised proteins and other molecules; this reaction, termed 'carnosinylation,' inhibits cross-linking of glycoxidised proteins to normal macromolecules; and carnosinylation could affect the fate of glycoxidised polypeptides. Studies on rat embryonic fibroblasts demonstrated that L-carnosine sustains the retention of cell morphology even during a nutritional insult for five weeks. Also, L-carnosine significantly reduces the formation of 8-hydroxy-deoxyguanosine (8-OH dG) in the cells after four weeks of continuous culture. Thus it could be inferred that the anti-senescent effect of L-carnosine is probably linked to its inhibition of formation of intracellular 8-OH dG during oxidative stress. Carnosine also extends cultured human fibroblast life-span, kills transformed cells, protects cells against aldehydes and an amyloid peptide fragment and inhibits, in vitro, protein glycation and DNA/protein cross-linking. Fibroblasts retain a juvenile appearance in the presence of carnosine, and revert to a senescent phenotype when carnosine is removed.

In addition to anti-glycation anti-oxidant activity, carnosine also has an anti-inflammatory action. Denatured protein at the site of inflammation is more susceptible to glycation, hence the anti inflammatory effect may enhance the inhibition of glycation.

Carnosine is water soluble and this suggests that it may represent the aqueous phase counterpart to lipid-soluble antioxidants such as α-tocopherol which act to protect cell membranes. Carnosine, and carnosine-related compounds (CRCs) (imidazole, histidine, anserine), and ergothioneine were found to be equally efficient in singlet oxygen quenching. During generation of hydroxyl radicals from hydrogen peroxide in the Fenton reaction, carnosine was found to be more effective than the CRCs tested. However, the following rank order of efficiency of carnosine-related compounds has been demonstrated while measuring the oxidation of human serum lipoproteins: acetylcarnosine<acetylanserine <homocarnosine=ophidine<carnosine<anserine whereas carnosine's component amino acids, histidine and alanine, have shown little or no inhibitory action against lipid or protein oxidation. Natural levels of carnosine decrease with age in parallel with the activities of other antioxidant systems such as superoxide dismutase (SOD) system. Additionally, carnosine itself can protect against peroxyl radical fragmentation of protein in Cu,Zn-SOD which would otherwise inactivate the enzyme. Carnosine is well known for its singlet oxygen quenching activity.

Carnosine has been shown to complex $Cu^{2+}$ dimerically, this may explain why carnosine reduces free radical production, as metal complexing will reduce available levels of $Cu^{2+}$ and $Fe^{2+}$ which would otherwise be coordinatively bonded by AGEs in proteins (the imidazole ring of carnosine can be compared with that of the many different imidazole containing AGE X-links) leading to hydroxyl and other reactive oxygen species production in situ. Carnosine also interferes with iron/ascorbate induced phospholipid oxidation.

Carnosine produces dose-dependent vascular relaxation (vasodilation) that is independent of endothelium. Interestingly, in the same study, carnosine's component amino acids L-histidine and alanine have been found to produce no effect and dose dependent vasoconstriction respectively.

Carnosine is hydrolysed physiologically into its component amino acids: histidine and β-alanine. β-alanine is believed to have be involved in the promotion of collagen synthesis. Histidine is known for its anti-inflammatory properties, its ability to scavenge single oxygen and interfere with redox reactions involving iron and other metal ions.

Carnosine has been shown to improve the rates of wound healing when given as part of a complete enteral formula, but has not to date been reported to be used topically in wound healing preparations.

CRCs such as the carnosine pro-drug N-acetyl-L-carnosine (NAC) undergo hydrolysis yielding carnosine in situ. NAC has been shown to treat oxidative stress in ocular disorders such as cataracts and glaucoma.

Other carnosine homologs include homocarnosine and anserine which protect Cu,Zn-SOD from inactivation and prevent release of $Cu^{2+}$. Many carnosine homologs are produced by the enzyme carnosine synthetase.

Functional homologs, derivatives and pro-drugs of carnosine that may be incorporated into compositions according to the invention include one or more of β-alanylhistamine (carcinine), N-acetyl-β-alanylhistamine (N-acetyl carcinine), L-prolyl histamine, and/or n-acetyl-L-carnosine.

Decarboxylation of L-carnosine provides a derivative with increased resistance to hydrolytic enzymes. Carnosine peptidomimetics (functional homologs) are known, which have free radical scavenging and lipid hydroperoxide deactivating properties similar to or even better than the natural carnosine peptide.

Two carnosine peptidomimetics (functional homologs) N-acetyl-β-alanylhistamine and L-prolylhistamine are highly effective inhibitors of lipid hydroperoxide-mediated cross-linking of a protein. In vivo, N-acetyl-β-alanylhistamine has been shown to protect skin enzymes from UV-induced degradation.

A composition according to the invention comprises one or more anti-oxidant(s), preferably selected from the group comprising: arginine, ascorbic acid, a prodrug or derivative of ascorbic acid, ascorbyl palmitate, magnesium ascorbyl phosphate, trisodium ascorbyl phosphate, anserine, carnosine, opidine, homocarnosine and/or acetylanserine. Generally, the or each anti-oxidant is present at from about 0.5 to 5%, preferably from about 1 to 3% w/w of the composition.

Arginine is a powerful antioxidant and a very effective sacrificial target for Maillard type protein cross-linking reactions. Both arginine and lysine have been shown to be effective inhibitors of glycation, but arginine especially tends to form AGEs itself. It is known that the number and diameter of capillary loops close to the dermal-epidermal junction (DEJ) is reduced with age. The supply of nutrients and removal of by-products from metabolism and other cellular processes is consequently impaired. L-arginine acts as a vasodilator due to enzyme-catalysed formation of nitric oxide (NO) in situ. The formation of nitric oxide (NO) from L-arginine is now recognized as a ubiquitous biochemical pathway involved in the regulation of the cardiovascular, central, and peripheral nervous systems, as well as in other homeostatic mechanisms.

Ascorbic acid (vitamin C, AA) is an essential nutrient involved in many physiological functions. It readily (yet reversibly) undergoes two consecutive, one-electron oxidation processes to form the ascorbate radical, a relatively unreactive free radical, and is therefore considered an excellent reducing agent. In living organisms, ascorbic acid can protect tissues and cells against oxidative damage by free radicals and reactive oxygen-derived species. AA is known to exert a strong UVA protecting ability in studies on eye lens proteins including X-ray irradiation.

Unfortunately, in some situations, ascorbic acid in solution can undergo oxidation and produce dehydro-L-ascorbic acid as well as many degradation products, which can result in browning of compositions containing ascorbic acid. Several factors can accelerate ascorbic acid degradation such as high storage temperatures, light, high pH values and the presence of dissolved oxygen, although the reaction mechanism of ascorbic acid with an oxygen molecule has not yet been fully elucidated. Moreover, the reaction of ascorbic acid with oxygen is strongly catalysed by metal ions, particularly cupric and ferric ions. To avoid degradation, the ascorbic acid component of a composition can be provided separately and mixed into the other components of the composition shortly before use. A stable prodrug or derivative of ascorbic acid can be included in the composition as an alternative, or in addition to, ascorbic acid.

Ascorbyl palmitate is a fat-soluble derivative of vitamin C widely used in skin care products. It is non-irritating and more stable than ascorbic acid. Furthermore, ascorbyl palmitate is a fat-soluble antioxidant and is at least as effective as vitamin E in protecting the skin from lipid peroxidation (a key type of free radical damage in the skin).

Magnesium ascorbyl phosphate is a water-soluble derivative of vitamin C. It is non-irritating and more stable than vitamin C. Most importantly, magnesium ascorbyl phosphate appears to have the same potential as vitamin C to boost skin collagen synthesis but is effective at significantly lower concentrations. Most vitamin C formulas are highly acidic and therefore produce exfoliation, so magnesium ascorbyl phosphate is a preferred ascorbic acid derivative for use in compositions, particularly those for individuals with sensitive skin and those wishing to avoid exfoliating effects.

Trisodium ascorbyl phosphate (Stay-C® 50) is the sodium salt of the monophosphate ester of ascorbic acid. It is a pro-vitamin, with greater stability in aqueous solution than ascorbic acid. Phosphatases in the skin act on trisodium ascorbyl phosphate to release ascorbic acid.

Compositions according to the invention may contain one or more substances capable of inducing expression of a molecular chaperone, particularly useful are substances capable of inducing expression of a heat shock protein, clusterin and/or alpha crystallin. The one or more substance capable of inducing expression of a molecular chaperone can be acetyl salicylic acid, salicylic acid, zinc ions, a zinc salt, zinc sulphate, and/or zinc-L-carnosine. Usually, a zinc containing agent is present at from about 0.1 to 1%, preferably from about 0.25 to 0.75%, most preferably around 0.5% w/w of the composition. When acetyl salicylic acid or salicylic acid is present in the composition a suitable concentration is from about 0.5 to 2.5%, preferably from about 1 to 1.5% w/w of the composition.

A composition according to the invention may further comprise one or more anti-apoptotic substance, preferably selected from the group comprising nicotinoamide, L-carnitine, acetyl-L-carnitine, N-acetyl-cysteine and/or L-carnosine. The or a anti-apoptotic substance is usually present at a concentration of from about 0.5 to 5%, preferably 1 to 3% of the composition.

In a fourth aspect, the present invention provides a composition comprising one or more substance capable of inducing expression of a molecular chaperone and a dermatologically acceptable excipient.

A composition according to the invention may further comprise one or more ingredient selected from the group comprising one or more vitamins, one or more small peptide(s), and/or one or more amino acid(s) or a derivative or prodrug thereof.

Vitamins that may be incorporated into compositions of the invention include vitamin B compounds such as thiamine (vitamin B1), e.g. as thiamine pyrophosphate, such as benfotiamine; pyridoxamine (vitamin B6), vitamin A and/or E, or a derivative or prodrug thereof.

Pyridoxamine (B6) has been shown to effectively inhibit AGE and lipoxidation product formation, and in particular blocks formation of methylglyoxal-lysine dimer by itself forming methylglyoxal-pyridoxamine dimer. Pyridoxamine (B6) and thiamine pyrophosphate (B1) have both been shown to be effective post-Amadori inhibitors of AGE formation with B6 effecting a measurable decrease in rate of AGE formation and final AGE levels and B1 effecting a measurable decrease in final AGE levels only. Both compounds show far greater potency in post-Amadori inhibition of AGE formation than aminoguanidine. Thiamine derivatives such as benfotiamine (lipid-soluble prodrug of thiamine) have been identified as potential therapeutic agents in the inhibition of intracellular glycation in the treatment of vascular diabetic complications and have been shown to inhibit imidazolone-type AGE accumulation.

The composition may comprise one or more small peptide(s) suitably as a dipeptide, tripeptide and/or tetrapeptide, and/or one or more amino acid(s), e.g. proline, lysine, histidine, alanine, or a derivative or prodrug thereof.

A composition according to the invention may further comprise one or more polysaccharide, which may be one or more proteoglycan, such as a glycosaminoglycan.

The one or more glycosaminoglycan employed can be a low and/or high molecular weight hyaluronan, chondriotin sulphate, dermatan sulphate and/or one or more derivative(s) thereof.

In addition to the need to deglycate matrix proteins and increase the vascular function of the dermis, an important effect of compositions according to the present invention is the re-establishment of the proteoglycan content and distribution. Proteoglycans (PGs) are important for providing the 'smooth' turgidity of skin due to hydration and are also important as intercellular reservoirs for growth factors and other cytokines. PGs are synthesized by the dermal fibroblasts and have a close relationship with growth factors such as basic fibroblast growth factor (b-FGF). The N-terminal binding domain of collagen is affected by glycation and consequently the quantity and location of PGs in the dermis are affected by AGE accumulation. For example, heparan sulfate proteoglycans (HSPGs) promote cellular proliferation through interaction with FGF-2.

Some GAGs, especially Hyaluronic acid, have been shown to be decreasingly present in ageing skin. Even though the mucopolysaccharides only constitute 0.1-0.3% of the dry weight of the skin, any decrease can be easily understood to influence the skin turgor as the molecules bind water in the dermis up to 1000 times the volume of the molecule itself. Additionally, these substances are known to influence migration, growth and differentiation of connective tissue cells in some instances.

Hyaluronic Acid or Hyaluronan ("HA") is a long-chained polysaccharide that is a major constituent surrounding cells in most animal tissues. HA is attracted to and adheres to specific receptors on cell membranes which can be found in increasing numbers at sites of damage and disease in the body with a significant amount on the skin. This means that drugs can potentially be targeted to and held at the site where the drug is needed. The safety profile of HA, its ability to carry drug and its potential targeting characteristics make it an excellent vehicle for topical drug delivery. Drugs can be covalently attached to HA or contained within the X-linked networks of derivatives of HA.

Hyaluronan has been used for decades in cosmetics, viscosurgery and viscosupplementation without immunological reactions or any other side-effects. It is present naturally at high concentrations in connective tissues such as skin and cartilage, in the vitreous body of the eye and in synovial fluid. Mostly it is bound to cells and proteins but some HA is present in the interstitial fluid. HA is a polysaccharide consisting of alternating units of glucuronic acid and N-acetylglucosamine. The carboxyl groups present are largely ionised at the pH of the skin (generally around pH 4.5 to 5.5) and it is therefore highly hydrophilic. The water binding properties and polymeric molecular size of HA predispose HA to forming viscoelastic gels which have potential for surface retention, acting as a reservoir for therapeutic agents. Despite the hydrophilic properties of HA, it can penetrate normal epidermis and accumulate extracellularly in the dermis before disposal via known metabolic pathways.

In preferred embodiments, a composition according to the invention will comprise a low and high molecular weight hyaluronan and/or one or more derivative(s) thereof. Low molecular weight hyaluronan characteristically has a molecular weight of less than $1\times10^6$ Da, whereas a high molecular weight hyaluronan generally has molecular weight of greater than $1\times10^6$ Da.

HA forms a viscoelastic, smooth, lubricating film when applied to the surface of the skin, thus externally applied HA not only has a beneficial effect on the skin, but also can be used to enhance the viscosity of a composition so that on application to the skin it remains in contact with the skin in a gel-like layer. This is particularly beneficial when ultrasound is to be applied to skin treated with a composition according to the invention.

The HA molecule can be derivatised via modification of the acetamido, the reducing end group but most commonly the hydroxy and carboxylate groups. The glycosidic bond is also readily hydrolysed to create shorter chains or oligosaccharides. HA-drug adducts have been synthesised for controlled delivery applications and HA-protein adducts as biomaterials and cell substrates.

HA exists as Na—HA at physiological pH. It has a complete lack of immunogenicity which makes it an ideal building block for biomaterials and drug delivery systems. HA effects a controlled and sustained release of drugs through the skin by the formation of a reservoir of the drug around the basement membrane. Neither NaCMC (at a weight or rheologically equivalent concentration) nor chondroitin sulphate (at a weight equivalent concentration) exert the controlled release effect seen for the hyaluronan formulation in full thickness skin, thus HA is a particularly preferred glucosaminoglycan for the purposes of the present invention. The enhancement of percutaneous absorption by HA is believed to be partly due to its ability to hydrate the skin so disrupting the compact cell/lipid layers. HA is superior to other GAGs in this respect due to its high water binding capacity.

Tetrasaccharides of HA have been found to exert an anti-apoptotic effect as they up-regulate HSP72 expression under conditions of stress and suppress cell death. High molecular weight HA polysaccharides are generally space filling molecules with anti-angiogenic, anti-inflammatory and immunosuppressive activity. Lower molecular weight fragments (6-20 kDa) are angiogenic, inflammatory and immunostimulatory.

HA has been shown to be depolymerised by Maillard reaction products (glucose-lysine) via a free-radical mechanism. Hydroxyl radicals depolymerise HA and have been linked to inflammation in arthritis and the breakdown of synovial fluid. High (but not low) molecular weight HA and derivatives of HA such as BEHA act as antioxidants scavenging reactive oxygen species (ROS) such as $O_2^-$ and OH, which otherwise would impair the migratory and proliferative properties of dermal fibroblasts thereby prolonging inflammation and delaying wound healing.

Hyaluronans have the ability to increase proteoglycan synthesis, stimulate tissue inhibitor of metalloproteinase-1, has the ability to stimulate collagen remodelling, to enhance cell migration, stimulates wound healing by upregulating the expression of transforming growth factor-β.

Low-molecular weight HA (~300 kDa) is available from Sigma, Poole, Dorset (isolated from bovine vitreous humor). High molecular weight HA is available from ConvaTec, Flintshire, UK (isolated from human umbilical cord). Commercially available HA preparations are given in tables 1a, 1b and 1c.

TABLE 1a

Examples of NaHA used in the clinical treatment of osteoarthritis

| Trade name | Molecular weight of NaHA* | Manufacturer |
|---|---|---|
| Artz ® | 600,000-1,200,000 | Seikagaku (Japan) |
| Hyalgan ® | 500,000-730,000 | Fidia (Italy) |
| Synvisc ® | mildly cross-linked HA | Biomatrix (USA) |

TABLE 1b

Examples of NaHA used in ophthalmologic surgery

| Trade name | Molecular weight of NaHA* | Manufacture |
|---|---|---|
| Opegan ® | 600,000-1,200,000 | Seikagaku (Japan) |
| OpeganHi ® | 1,900,000-3,900,000 | Seikagaku (Japan) |
| Healon ® | 1,900,000-3,900,000 | Pharmacia-Upjohn (Sweden) |
| Opelead ® | 1,530,000-2,130,000 | Shiseido (Japan) |

*Molecular weight of active ingredient

Other HAs include NIF—NaHA marketed under the name of Healon® for medical and Hylartil® for veterinary use; Hylan A (elastoviscous fluid) and Hylan B (viscoelastic gel) developed by Biomatrix Inc.

TABLE 1c

| Trade Name (manufacturer) | Generic Name | Molecular Weight ($\times 10^6$ Da) | Elasticity (%) @ 3 Hz | Complex viscosity (Pa s @ 0.02 Hz) | Polysaccharide concentration (mg/ml) |
|---|---|---|---|---|---|
| Hyalgan ® (Fidia) | Hyaluronan | 0.5-0.65 | 26 | <0.1 | 10 |
| Artz ® (Seikagaku) | Hyaluronan | 0.75 | 33 | 0.3 | 10 |
| Orthovisc ® (Anika) | Hyaluronan | 1.5 | 66 | 42 | 15 |
| Synvisc ® Biomatrix | Hylan | 6 | 88 | 213 | 8 |
| SkyePharma (Solareze diclofenac gel) | | 0.6 | | | |

A dermatogically acceptable excipient or excipients suitable for use in a composition according to the invention include water, a water/ethanol mixture (e.g. up to 25%, preferably up to 20% ethanol in the composition % w/w), a viscous gel or emulsion, an aqueous gel, a hydrogel, a water-based emulsion in the form of a cream or application, an oil-in-water emulsion in the form of a cream or application, or a jelly.

Generally, a composition which is to be applied in conjunction with ultrasound treatment (where the composition is applied prior to, during ultrasound treatment, or shortly after an ultrasound pre-treatment), will have a viscous nature, so that a layer of the composition can be spread on the skin and will remain in place on the skin until it is removed, e.g. by wiping the composition away with tissue or cotton wool, or by rinsing the formulation off.

A composition according to the invention may comprise a film-forming ingredient. One or more ingredient selected from: a sun block, humectant, pigment, foundation or concealer pigment, fake tan pigment or composition may be included in a composition according to the invention.

A composition according to the invention is preferably at a pH close to the pH of skin, e.g. at a pH of from pH 4 to pH 6, or pH 4.5 to pH 5.5.

In a fifth aspect the present invention provides a method for treatment of the skin, comprising applying to the skin a composition according to the invention.

Preferably the method is a method of cosmetic treatment of cosmetic skin conditions. However the invention also encompasses the treatment of medical skin conditions, in which instances the method is a method of medical treatment.

A method for treatment of the skin may further comprise application of ultrasound directly or indirectly to an area of skin to which the composition has been applied, or as a pre-treatment to an area of skin to which the composition is to be applied.

In preferred methods of the invention application of ultrasound is performed at low and/or high frequency, directly or indirectly to an area of the skin where the composition has been applied, or is to be applied.

Low and high frequency ultrasound can be applied simultaneously, sequentially or separately, e.g. sequentially as several alternating single applications of low and high frequency or, separately where a series of applications of low frequency is alternated with a series of applications of high frequency. Low frequency ultrasound is believed to be useful to facilitate delivery of molecules to the skin (a process termed "sonophoresis"). High frequency ultrasound has a lesser sonophoretic effect than low frequency, but it also has many other effects beneficial to the skin in that it stimulates fibroblast proliferation, stimulates collagen and other extracellular matrix (ECM) component formation (e.g. fibrillin), stimulates blood supply, renews the elastic quality of ECM which stiffen with age, stimulates the expression of Heat Shock Proteins (HSPs—intracellular molecular chaperones) in fibroblasts (dermis) and keratinocytes (epidermis) through thermal and mechanical stimulation.

In a preferred method, low and high frequency ultrasound is applied simultaneously.

In methods of the invention involving application of low and high frequency ultrasound, the low frequency component of the ultrasound is preferably applied in continuous mode and the high frequency component is preferably applied in pulsed mode.

The term "ultrasound" describes sound frequencies of 20 kHz and above, a low ultrasound frequency is from 20 to 500 kHz, the spatial average power density of the low frequency ultrasound energy being from 20 to 500 mW/cm$^2$; a high ultrasound frequency is from 500 kHz (0.5 MHz) to 3.5 MHz, the spatial average power density of the high frequency ultrasound energy being from 0.5 to 3 W/cm$^2$.

In methods of the invention generally the beam is not focussed and is diverging. The target rise in skin temperature is up to 42 or 43° C., but preferably no higher. Single areas of skin are insonated for a minimum of 5 minutes, preferably 10 minutes, or a time between 5 and 12 minutes.

In methods of the invention, ultrasound can be applied using a hand-held applicator, optionally adapted for application of a composition according to the invention to the skin. For example, a cartridge/dispenser can be attached to the ultrasound head such that the formulation is gradually released as the head is moved around the skin surface, the cartridge may contain a pre-set amount of formulation. Different cartridges with different formulations can be attached depending on the skin condition being treated, e.g. different cartridges may contain different compositions for anti-ageing treatments, the treatment of scars, stretch-marked skin or cellulite. The ultrasound is applied by gently massaging the ultrasound applicator on the skin in a circular or linear stroking movement.

Ultrasound can be applied as a pre-treatment, before application of a composition of the invention. Alternatively or additionally, a layer of the composition or a material impregnated with the composition can be applied to the skin during or prior to the application of ultrasound. When using an applicator, the applicator is moved across the skin so that no single area is over-exposed to ultrasound, which could cause overheating. The combination of ultrasound and the mechanical stimulus afforded by the massaging action helps to stimulate the skin to encourage renewal and repair.

Ultrasound can be applied by applied by immersion of the area to be treated in an ultrasound bath, e.g. directly by immersing bare skin in a composition of the invention, or by coating the skin with the composition, wrapping the part to be treated, and immersion in a liquid that can transmit ultrasound energy.

As described above, an apparatus for application of ultrasound to the skin may comprise a plurality of ultrasound transducer elements arranged as an array in a flexible material in spaced configuration, wherein the ultrasound transducer elements are capable of delivering ultrasound at low and/or high frequency to an area of the skin.

Skin treatment using these method can be performed in a beauty clinic or in a medical clinic such as a hospital clinic, or in a doctor's surgery.

A circular area of skin 2 to 3 cm in diameter should be subjected to ultrasound for a minimum of 5 minutes, preferably 10 minutes or a time between 5 and 12 minutes.

Where skin treatments are to be carried out in a beauty clinic, or a medical clinic, such as in a hospital or doctors surgery, a suitable ultrasound device for use in methods of the invention is an ultrasound array incorporated into a mask or patch as described herein; or a device which can generate low and high frequency outputs and has a handset designed to give combinations of output frequencies and energies, such as the Duo Son™ unit (Orthosonics, Devon UK). The Duo Son™ unit can be used either at the current specification (described in Table 2), or at a slightly altered specification dictated by optimisation of frequency, wattage and duty cycle parameters to enhance actives delivery and cell/protein stimulation. Such adjustments remain within the guidelines for CE marking of the unit.

The effectiveness of ultrasound (US), or sonophoresis for delivery of molecules to the skin, is due to two aspects of its action on the skin. Firstly, cavitation results from the rapidly oscillating pressure field causing bubble formation and collapse which mechanically creates channels through the stratum corneum. The second effect is actual direct heating of material through which the sound waves are travelling due to attenuation of the acoustic energy through reflection, absorption and dispersion. This occurs in skin up to four times more than in other tissues due to its heterogeneity. Heating is known to disrupt the lipid bilayer system in the stratum corneum also contributing to the enhanced permeability of the epidermis.

TABLE 2

| Power Supply | |
|---|---|
| Input | 90 V 260 V ac (50/60 Hz) |
| Output | 24 V, 1.25 A dc |
| Battery life | 15 mins to 2 hours depending upon mode selection |

| Other | |
|---|---|
| Modes | LF only, LF + HF (pulsed) |
| Weight | 2 kg |
| Dimensions | 200 × 250 × 70 mm (w × d × h) |
| Class | BF |
| Display | Liquid Crystal Display |
| Standard | IEC 61689 (96) |

|  | Low Frequency 45 kHz | High Frequency 1 MHz |
|---|---|---|
| Effective beam radiating area | 16.3 cm$^2$ | 0.38 cm$^2$ |
| Beam non-uniformity ratio | <6 | <6 |
| Beam Type | Diverging | diverging |
| Power Settings | 0.15 W, 0.4 W, 0.75 W | 0.07 W, 0.14 W |
| Maximum Intensity | 100 m W/cm$^2$ | 1 W/cm$^2$ (420 mW/cm$^2$ pulse averaged) |
| Mode of Operation | Continuous | pulsed 20% duty cycle |

Essentially the skin's permeability is increased by disruption of the intercellular lipids through a combination of heating and/or mechanical stress and through the increase in porosity. Temperature rises to 50° C. (20 kHz, 10-30 W/cm$^2$) have been reported, but rises as little as 11° C. (1 MHz, 2 W/cm$^2$) have been shown to cause skin damage. Continuous mode ultrasound at an intensity of 1 W/cm$^2$ raises the temperature of tissue at a depth of 3 cm to 40° C. in 10 minutes. It has been suggested that tissue must reach a temperature of 40-45° C. for at least 5 minutes to be therapeutically beneficial. Tissue temperatures have been shown to increase at a rate of 0.86° C./min when exposed to 1 W/cm$^2$-1 MHz ultrasound.

Ultrasound is known to act to degrade polymers and has been used to increase in the release of incorporated drugs from these polymers. When ultrasound is applied to compositions of the invention comprising polymers such as polysaccharides, preferably proteoglycans, in particular glucosaminoglycans, such as HA, the ultrasound will degrade (depolymerise) the polymer. This has a number of effects, when HA is present in the composition, ultrasound generates shorter chain HA polymers that are more readily able to penetrate the skin. In addition to employing ultrasound to facilitate permeation of active substances, it is important that the effective residence time of such actives at the site of action is maximised. The microvasculature enables substances to be removed from the site of permeation for breakdown in the liver. Optimisation of the residence time is necessary to permit the active substance to have the desired effect. When composition of the invention comprise polymers such as polysaccharides or proteoglycans, in particular glucosaminoglycans, such as HA, ultrasound treatment will assist in formation of a depot of the polymer (e.g. HA) within the skin which can act as a reservoir for slow release of actives providing an extended duration of effect.

Ultrasound also stimulates liberation of the active ingredients of the composition. Ultrasound will also act to depolymerise polymers polysaccharides or proteoglycans, in particular glucosaminoglycans, such as HA that have penetrated the skin. When HA and ascorbic acid are present in a composition, depolymerisation of the HA will be encouraged by ascorbic acid in which will react with atmospheric oxygen and stimulate depolymerisation.

A composition of the invention can be applied in conjunction with ultrasound, but this is not essential, a composition of the invention may also be applied to the skin without the application of ultrasound. In a preferred method for treatment of skin, a first composition of the invention is applied in conjunction with ultrasound (either with an ultrasound pre-treatment of the skin to which the composition is applied, or with ultrasound treatment of skin during or after application of the composition to the skin) on a weekly, fortnightly or monthly basis. Following the ultrasound treatment of the skin, a second composition of the invention may be applied, e.g. on a daily or 12 hourly basis without the need for ultrasound. The first and second compositions can be identical or may differ in composition, but will both be compositions according to the invention.

The present invention further provides a dressing comprising a composition according to the invention, which may be presented in the form of a plaster, patch, gel patch bandage or foam.

Also provided is a kit comprising a composition according to the invention and optionally, a device comprising an ultrasound source and/or optionally an applicator for applying ultrasound to the skin and/or for applying the composition to the skin. A kit according to the invention is suitable for performing a method of the invention as described herein. A kit may further comprise instructions for use of the kit.

The invention provides the use of a composition according to the invention in the treatment of a cosmetic skin condition. Also provided is the use of composition according to the invention in the manufacture of a cosmetic composition for the treatment of a cosmetic skin condition e.g. selected from the group: scarring, sun damaged skin, ageing skin, wrinkles, coarseness, irregular pigmentation, telangiectasias, elastosis, cellulite, orange peel appearance of skin; dry skin conditions, scaliness, acne, stretch marks; rashes, chapping, inflamed skin; blemishes, rosacea, acne ice-pick scars, hypertrophic and keloid scars, and hairloss.

The term "cosmetic skin conditions", as used herein, includes signs of skin ageing which include, but are not limited to, all outward visibly and tactilely perceptible manifestations as well as any other macro or micro effects due to skin ageing. Such signs may be induced or caused by intrinsic or extrinsic factors, e.g., chronological ageing and/or environmental damage (e.g., sunlight, UV, smoke, ozone, pollutants, stress, etc.). These signs may result from processes which include, but are not limited to, the development of textural discontinuities such as wrinkles, including both fine superficial wrinkles and coarse deep wrinkles, skin lines, facial frown lines, expression lines, rhytides, dermatoheliosis, photodamage, premature skin ageing, crevices, bumps, pits, large pores (e.g., associated with adnexal structures such as sweat gland ducts, sebaceous glands, or hair follicles), "orange peel" skin appearance, dryness, scaliness, flakiness and/or other forms of skin unevenness or roughness; excess skin oil problems such as over-production of sebum, oiliness, facial shine, foundation breakthrough;

abnormal desquamation (or exfoliation) or abnormal epidermal differentiation (e.g., abnormal skin turnover) such as scaliness, flakiness, keratosis, hyperkeratinization; inadequate skin moisturization (or hydration) such as caused by skin barrier damage, environmental dryness; loss of skin elasticity (loss and/or inactivation of functional skin elastin) such as elastosis, sagging (including puffiness in the eye area and jowls), loss of skin firmness, loss of skin tightness, loss of skin recoil from deformation; non-melanin skin discoloration such as under-eye circles, botching (e.g., uneven red coloration due to, e.g., rosacea), sallowness (pale colour), discoloration caused by telangiectasia; melanin-related hyperpigmented (or unevenly pigmented) skin regions; post-inflammatory hyperpigmentation such as that which occurs following an inflammatory event (e.g., an acne lesion, in-grown hair, insect/spider bite or sting, scratch, cut, wound, abrasion, and the like); atrophy such as, but not limited to, that associated with ageing or steroid use; other histological or microscopic alterations in skin components such as ground substance (e.g., hyaluronic acid, glycosaminoglycans, etc.), collagen breakdown and structural alterations or abnormalities (e.g., changes in the stratum corneum, dermis, epidermis, the skin vascular system such as telangiectasia); tissue responses to insult such as itch or pruritus; and alterations to underlying tissues (e.g., subcutaneous fat, cellulite, muscles, trabeculae, septae, and the like), especially those proximate to the skin.

The invention also provides the use of a composition according to the invention in a medical treatment or as a medicament. Thus a composition of the invention is provided for use as a medicament. Further provided is the use of a composition according to the invention in the manufacture of a medicament for the treatment of a medical skin condition, e.g. selected from the group: scarring, sunburn, wounds, cuts, bruises, burns, burn scarring, eczema, dermatitis, dry skin conditions, urticaria, psoriasis.

LIST OF FIGURES

FIG. 1 (a)-(c) show an array of transducer elements; FIG. 1(d) shows an individual transducer element with dual frequency capability.

FIG. 2 (a)-(b) show a transducer element.

FIG. 3 A shows a single DDS chip for generation of alternative high and low frequencies, whereas in FIG. 3 B high and low frequencies are generated in individual circuits.

EXAMPLES

Example 1 Topical Formulation "Topical 1"

Figure 1A:
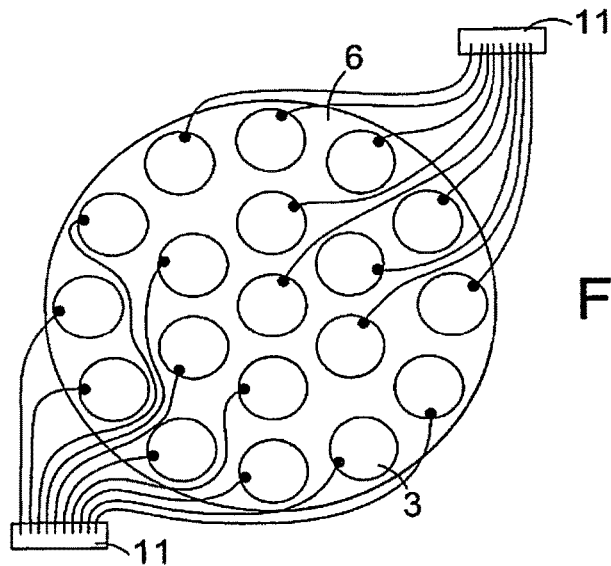
Figure 1B:
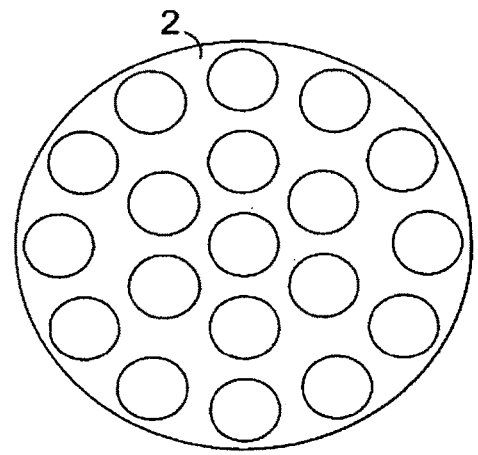
Figure 1C:
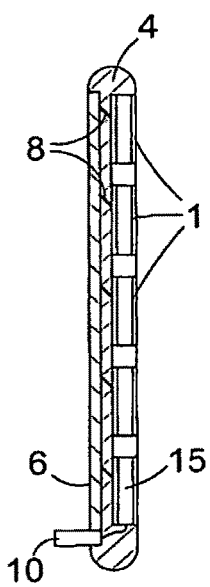
Figure 1D:
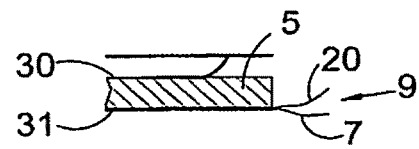
Figure 2A:
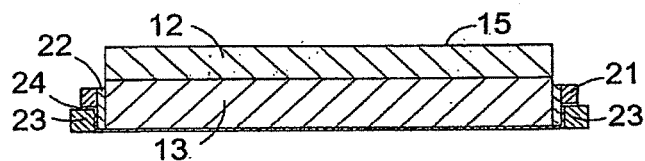
Figure 2B:
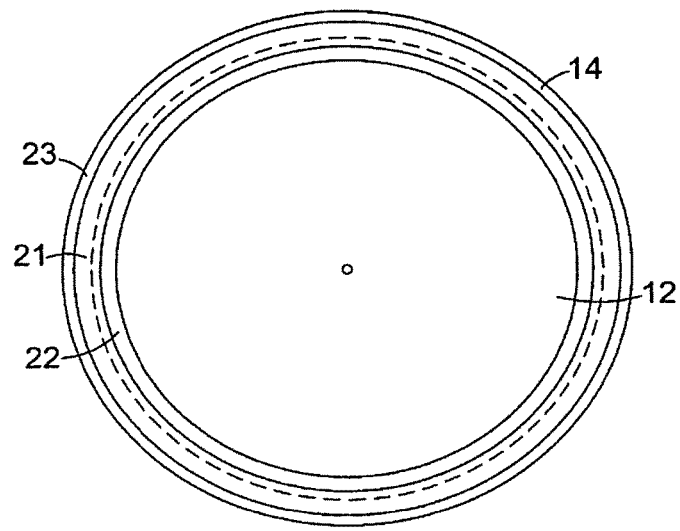
Figure 3:
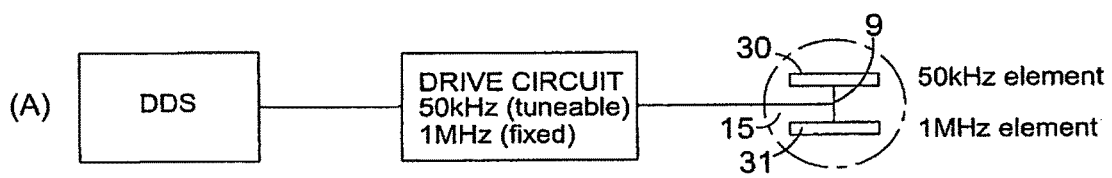
Figure 3:
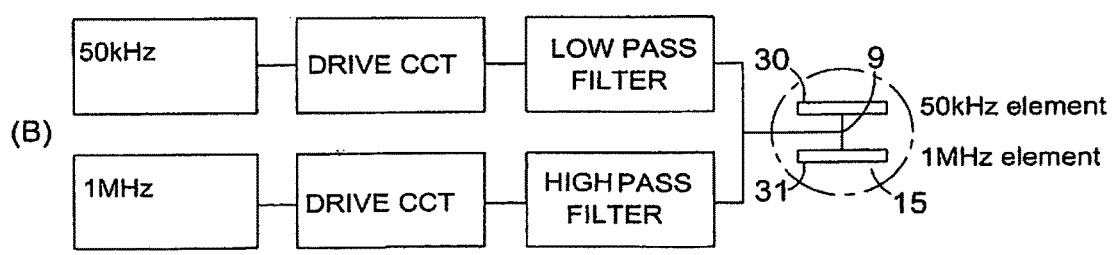

Topical 1 is a composition according to the invention containing the following components:

TABLE 3

| Component | Amount % w/w |
|---|---|
| Hyaluronic acid (0.8-3 MDa mol wt range) | 1% |
| Hyaluronic acid (1.5-1.8 MDa mol wt range) | 3% |
| Ethanol | 20% |
| Ascorbic acid | 3% |
| Trisodium ascorbyl phosphate (STAY C-50) | 1% |
| Carnosine | 3% |
| N-Acetyl Carnosine | 1% |
| Arginine | 3% |
| Sterile distilled water | to 100% |

Example 2 Patch Tests

The standard four-day patch test assay was extended to a seven-day period to examine the effect of the Topical 1 formulation under occlusion or delivered by ultrasound on the induction of fibrillin expression as a mechanism by which clinical signs of photoageing may be improved.

Subjects with clinical evidence of photoageing of forearm skin had the following products applied under occlusion to the dorsum of the forearm:
(1) 0.025% t-RA made up in a vehicle comprising 67.2% ethanol, 30% propylene glycol and 0.05% butyl hydroxytoluene (preservative) to 100% with deionised water (positive control),
(2) Vehicle alone as above,
(3) Topical 1 formulation.

Topical 1 was delivered with and without use of an ultrasound device.

The positive control, topical application of 0.025% all-trans RA with occlusion was applied within the standard four-day time frame to minimise potentially deleterious side effects.

Fibrillin is a major constituent of the elastin network in the papillary dermis and plays an important role in securing the epidermis to the underlying dermis. Topical application of all-trans retinoic acid (t-RA) as a positive control ameliorates the clinical signs of photoageing. Previous work has demonstrated that topical application of t-RA under occlusion for four days (the four-day patch test) produces a significant increase in fibrillin mRNA and protein, predictive of those seen after several weeks of non-occluded topical application providing a rapid and convenient means of assessing the action of new therapeutic interventions upon the skin.

Ageing can also be monitored by examination of other molecules within the skin. Previous work has identified alterations in the expression of the enzyme matrix metalloproteinase 1 (MMP-1; essential for extracellular matrix remodelling)[3] and in the nuclear retinoid receptor retinoic acid receptor α (RARα; necessary for modulating the effects of vitamin A and its derivatives)[4]. Two molecular chaperones were assessed to identify pathways for eliminating abnormal proteins; these were heat shock protein-72 (HSP72)[5] and the extracellular chaperone, clusterin[6].

The study was an open clinical study; assessment of biopsies was randomised and blinded. The study was carried out on 10 subjects, aged 40-80 years, who were judged to have moderate to severe photoaged forearm skin.

The inclusion criteria applied were:
Aged 40 to 80 years; willing to submit to examination of photoaged forearm skin; willing to wear test patches on forearm for up to 4 days; willing to submit to 3 mm punch biopsies from each of the four test sites (total of 4 biopsies); no disease state that would impair evaluation of the test sites; not on systemic drugs; no topical or systemic retinoids within the past 6 months and 12 months respectively prior to entry to the study; no topical steroids or other topical drugs two weeks; signed informed consent.

The exclusion criteria applied were:
History of use of experimental drug or experimental device in the 30 days prior to entry into the study; history of keloid scars; pregnancy or breastfeeding.

The study procedure involves taking of history and a physical examination; clinical grading of the severity of extensor forearm photoageing on a 0 to 9 scale (0=no damage; 9=maximum photodamage); written, witnessed, informed consent is obtained. Those subjects admitted to the study have photodamage grade of 6 or greater.

Materials and Methods
Patch-Test Protocol

Six healthy but photoaged female volunteers were recruited (age range 52-79 years). Test substances were applied separately under standard 6 mm diameter Finn chambers to the extensor aspect of the forearm: these were Topical 1 formulation (20 µl/chamber), vehicle base (20 µl/chamber) and 0.025% all-trans RA (Retin-A® cream, Janssen-Cilag Ltd., 20 µl/chamber). In addition, a baseline untreated biopsy was taken as a reference point. Formulations were applied to clean skin on days 1 and 4 of the assay. All-trans RA was applied to an untreated site on day 4. On day 8, Finn chambers were removed and 3 mm punch biopsies were obtained under 1% lignocaine anaesthesia from each of the test site. Biopsies were embedded in OCT compound (Tissue-Tek®, Miles, Ind., USA) and snap frozen in liquid nitrogen. Biopsy sites were sutured with 1×4/o ethilon and subjects instructed to return between 7-10 days for suture removal.

Ultrasound Protocol

Ten healthy but photoaged volunteers were recruited (men: 2; female: 8; age range 40-79 years). Topical 1 formulation was applied to extensor forearms alone and with the aid of an ultrasound device (Duo Son™ unit, Orthosonics, Devon UK). Low frequency (45 kHz, 100 mW/cm$^2$, continuous) and high frequency (1 MHz, 1 W/cm$^2$ pulsed average, pulsed 20% cycle) were applied simultaneously for a period of ten minutes, during which time the ultrasound delivery head was moved over the skin. Treatment occurred on days 1, 4 and 7 of the assay. On day 8, 3 mm punch biopsies were removed from each treatment site as described previously.

Slide Preparation

Frozen sections were prepared at a thickness of 10 µm (OTF cryostat, Bright Instruments Ltd.) and mounted onto gelatin-coated slides prior to histological analysis.

Immunohistochemistry

A number of extracellular matrix (ECM) molecules known to be reduced in photoaged skin were assayed by immunohistochemistry to detail the potential effects of the Topical 1 formulation and its method of delivery. The primary marker of outcome was the distribution of fibrillin-rich microfibrils proximal to the dermal-epidermal junction (DEJ). Also assessed were the number of epidermal keratinocytes expressing MMP-1 and RARα. Molecular chaperones, HSP72 and clusterin were examined to assess potential repair mechanisms.

For each analysis, the marker was identified in each of three sections (i.e., 3 sections/treatment/patient).

Sections were optimally fixed. Following hydration in tris-buffered saline (TBS; 100 mM Tris, 150 mM NaCl), sections were solublised by addition of 0.5% Triton®-X 100 (10 minutes). Following washing, endogenous peroxidase activity was abolished by incubation with an excess of hydrogen peroxide in methanol (30 minutes). Sections were blocked prior to application of primary antibody (overnight incubation at 4° C.). Negative controls were concurrently incubated with either block alone or control mouse serum. Following incubation, sections were stringently washed with TBS prior to application of an appropriate biotinylated secondary antibody. This was further conjugated to the enzyme horseradish peroxidase using a commercially available kit following the manufacturers instructions (ABC Elite System, Vector Laboratory, Peterborough UK). Antibody was localised using Vector SG® as chromogen (10 minute incubation, washing in TBS quenched this reaction. Sections were counterstained using Nuclear Fast Red and finally dehydrated through serial alcohols, cleared and permanently mounted.

TABLE 4

| Marker | Host | Clone | Fixation | Dilution |
|---|---|---|---|---|
| Fibrillin-rich microfibrils | Mouse IgG | NeoMarkers; 11C1.3 | 4% PFA | 1:100 |
| MMP-1 | Mouse IgG | Oncogene; 41-1E5 | 4% PFA | 1:100 |
| RARα | Rabbit IgG | Santa Cruz Biotechnologies | acetone | 1:100 |
| HSP72 | Mouse IgG | Stressgen Biotechnologies | 4% PFA | 1:100 |
| Clusterin | Rabbit IgG | Santa Cruz Biotechnologies | 4% PFA | 1:100 |

Quantification

Sections were randomised, blinded and examined on a Nikon OPTIPHOT microscope (Tokyo, Japan). For assessment of ECM components, the degree of immunostaining was assessed on a 5 point semi-quantitative scale where 0=no staining and 4=maximal staining. Four sections (including control) were examined per subject per site. The degree of immunostaining was scored for three high power fields per section, and the average score calculated for each site/test area.

For cell-associated staining, the numbers of positive epidermal keratinocytes were assessed per high powered field, and the average score calculated for each site/test area.

Differences in the distribution between the test sites, and after application of test substances for varying periods of time, were assessed for significance using the repeated measures analysis of variance test (ANOVA). To assess whether delivery methods affected outcome measures, data was tested using paired Student's t-tests. Both models were tested using SPSS+ software (v11.5, SPSS Inc., IL USA) with significance taken at the 95% confidence level.

Results
Erythema

All volunteers tolerated the patch test protocol well. Furthermore, all-trans RA produced marked erythema at the site of application. Erythema was not observed using the Topical 1 formulation.

Patch-Test Protocol
Fibrillin-1 IHC

Figure 4:
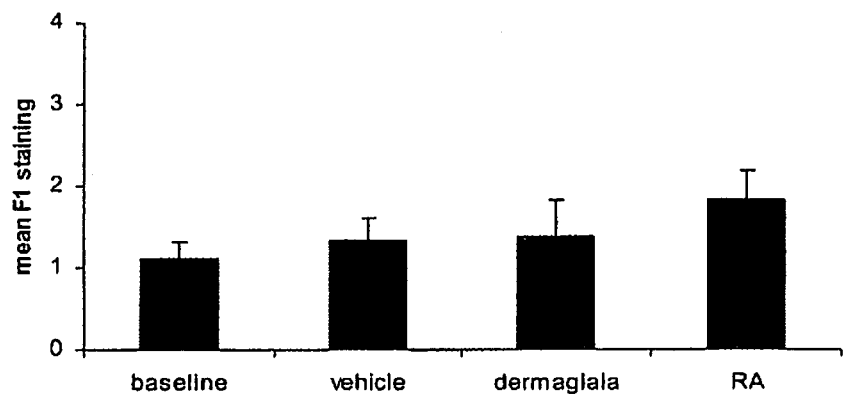
FIG. 4 shows the effect of Topical 1 formulation on fibrillin expression proximal to the dermal-epidermal junction.

Application of all-trans RA (our "gold" standard) produced deposition of fibrillin-1 proximal to the DEJ in 3/6 volunteers. The Topical 1 formulation resulted in increased fibrillin-1 deposition in 4/6 volunteers tested but to a lower level than that generally observed using all-trans RA (FIG. 4).

TABLE 5

| Fibrillin-1 staining Treatment | Mean | Std Deviation |
|---|---|---|
| Baseline | 1.1111 | 0.4608 |
| vehicle | 1.3241 | 0.6050 |
| Topical 1 formulation | 1.3704 | 0.9930 |
| All-trans RA | 1.8241 | 0.7985 | p > 0.05, non significant

MMP-1 IHC

Figure 5:
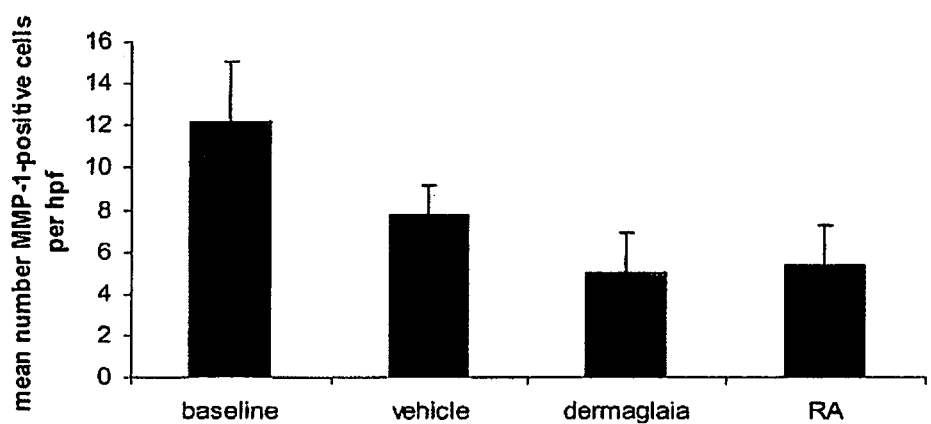
FIG. 5 shows the effect of Topical 1 formulation on MMP-1 expression in the epidermis.

MMP-1 staining was observed in both epidermis and dermis. Overall, topical application of all-trans RA for 4-d under occlusion reduced MMP-1 expression in epidermal keratinocytes, although this did not reach significance. Application of the Topical 1 formulation resulted in a similar level of reduction (FIG. 5).

TABLE 6

| MMP-1 staining Treatment | Mean | Std Deviation |
|---|---|---|
| Baseline | 12.1650 | 6.4340 |
| vehicle | 7.9890 | 3.2898 |
| Topical 1 formulation | 5.0093 | 4.2616 |
| All-trans RA | 5.3333 | 4.3165 | p > 0.05, non significant

RARα IHC

Figure 6:
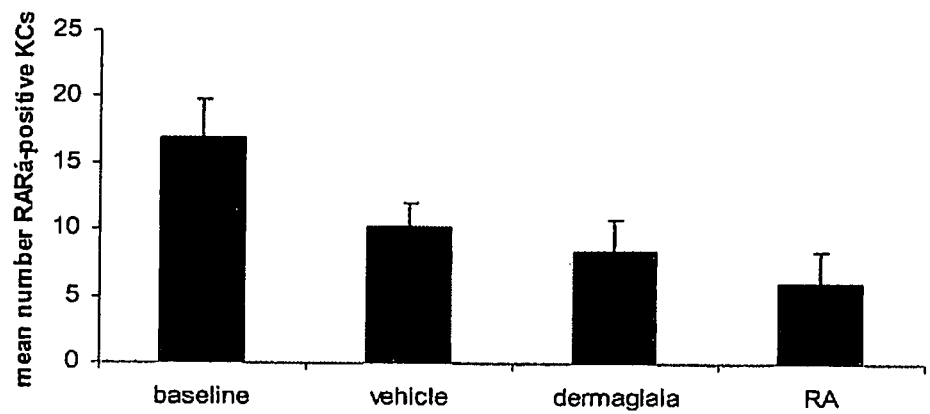
FIG. 6 shows the of Topical 1 formulation on RARα expression in the epidermis.

RARα staining was observed in primarily in the epidermis. Overall, topical application of all-trans RA for 4-d under occlusion significantly reduced RARα expression in epidermal keratinocytes. Application of the Topical 1 formulation resulted in a similar level of reduction, although this did not reach significance in this data set (FIG. 6).

TABLE 7

| RARα staining Treatment | Mean | Std Deviation |
|---|---|---|
| Baseline | 16.8370 | 6.7277 |
| Vehicle | 10.1111 | 4.1407 |
| Topical 1 formulation | 8.3611 | 5.1287 |
| All-trans RA | 6.0463 | 5.1090 | p > 0.05, non significant

HSP72

Figure 7:
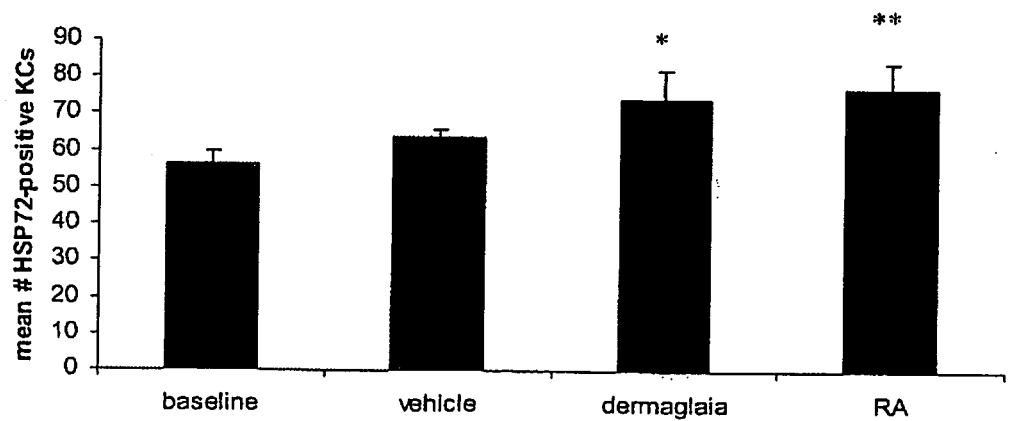
FIG. 7 shows the effect of Topical 1 formulation on HSP72 expression in the epidermis.

HSP72 is found mainly in the epidermis where strong staining was observed. Treatment with all-trans RA significantly increased the expression of epidermal HSP72 as did the Topical 1 formulation (p=0.005 and 0.012 respectively; FIG. 7).

TABLE 8

| HSP72 staining Treatment | Mean | Std Deviation |
|---|---|---|
| Baseline | 56.18 | 8.55 |
| Vehicle | 63.61 | 4.83 |
| Topical 1 formulation | 74.08* | 17.49 |
| All-trans RA | 77.03** | 15.44 |

*p = 0.012
**p = 0.005

Ultrasound Protocol
Fibrillin-1

Figure 8:
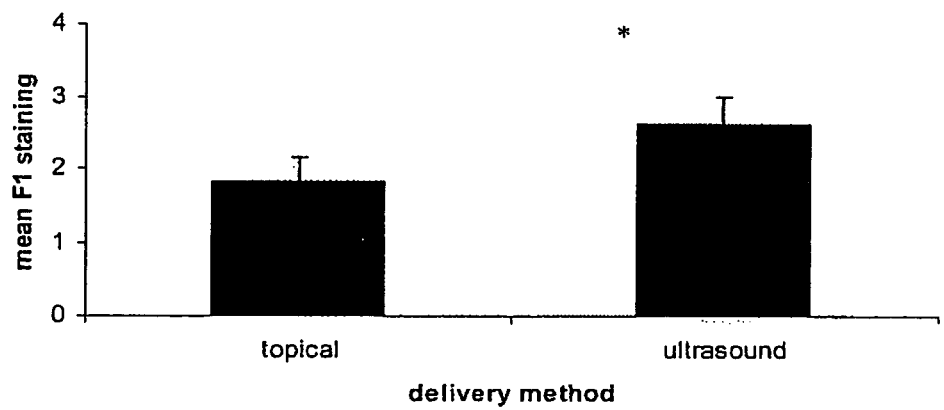
FIG. 8 shows the effect of Topical 1 formulation on fibrillin expression proximal to the dermal-epidermal junction following ultrasound treatment.

The Topical 1 formulation was further applied to photoaged extensor forearm by basic topical application without occlusion or via an ultrasound device. In all those studied (n=10) delivery by ultrasound resulted in significantly increased fibrillin deposition proximal to the dermal-epidermal junction (FIG. 8).

TABLE 9

| Fibrillin-1 staining Treatment | Mean | Std Deviation |
|---|---|---|
| Topical | 1.8272 | 0.8698 |
| Ultrasound | 2.6065* | 1.0052 |

*p = 0.033

Figure 9:
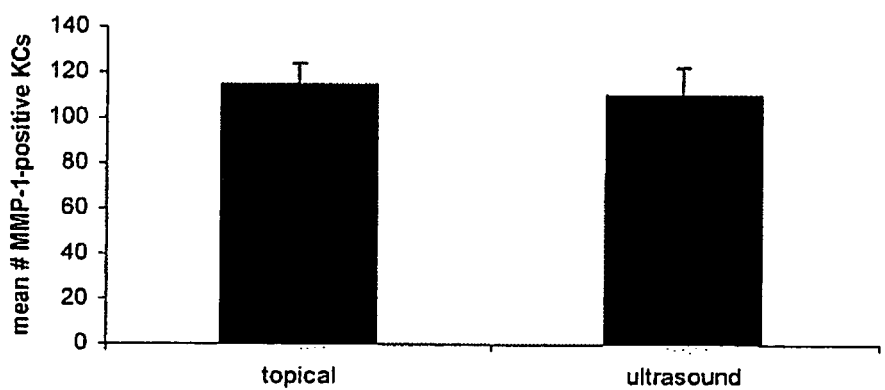
FIG. 9 shows the effect of Topical 1 formulation on epidermal MMP-1 expression following ultrasound treatment.

MMP-1 staining was observed in both epidermis and dermis. There was a slight, non-significant, reduction in MMP-1 expression in epidermal keratinocytes following ultrasound treatment (FIG. 9).

TABLE 10

| MMP-1 staining Treatment | Mean | Std Deviation |
|---|---|---|
| Topical | 114.71 | 22.03 |
| Ultrasound | 107.46 | 31.96 | p > 0.05, non significant

HSP72

Figure 10:
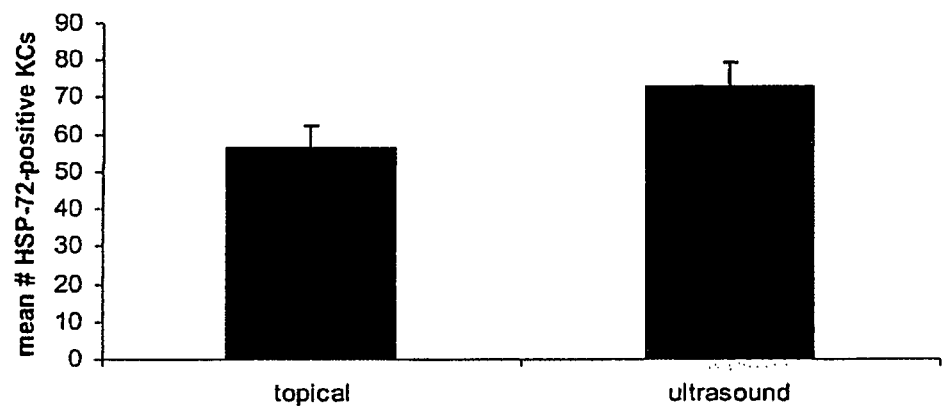
FIG. 10 shows the effect of Topical 1 formulation on epidermal HSP72 expression following ultrasound treatment.

HSP72 showed a slight, but non-significant, increase in epidermal expression following ultrasound treatment (FIG. 10).

TABLE 11

| HSP72 staining Treatment | Mean | Std Deviation |
|---|---|---|
| Topical | 56.31 | 16.58 |
| Ultrasound | 67.57 | 16.41 | p > 0.05, non significant

Clusterin

Figure 11:
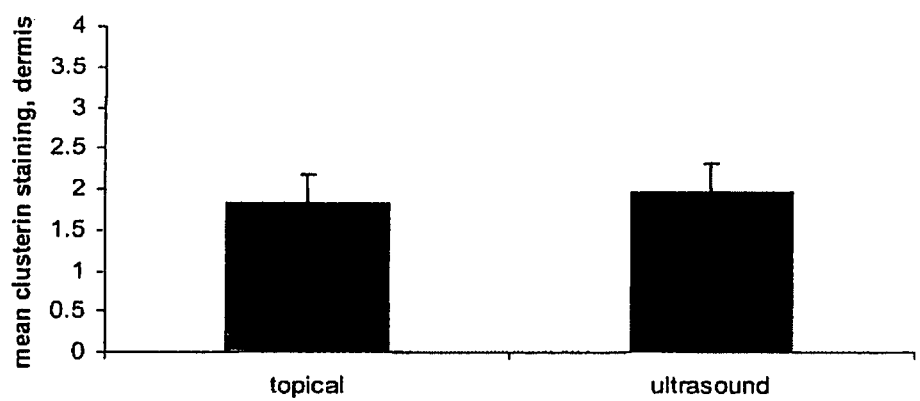
FIG. 11 shows the effect of Topical 1 formulation on dermal clusterin expression following ultrasound treatment.

Clusterin also showed a slight, but non-significant, increase in dermal expression following ultrasound treatment (FIG. 11).

TABLE 12

| Clusterin staining Treatment | Mean | Std Deviation |
|---|---|---|
| Topical | 1.80 | 0.98 |
| Ultrasound | 1.95 | 1.00 | p > 0.05, non significant

Summary

Application of the Topical 1 formulation using an ultrasound device significantly increased fibrillin deposition proximal to the dermal-epidermal junction of photoaged skin.

HSP72 expression was modulated by both the Topical 1 formulation and all-trans RA. Furthermore, ultrasound delivery of Topical 1 formulation also resulted in increased HSP72 expression. It is possible that increased heat shock protein expression may be beneficial to the skin, by 'priming' cells to cope with environmental stressors (hormesis). Hence, increased HSP72 expression by epidermal keratinocytes may be involved in cellular repair processes following damage.

The data suggests that there is reduction in MMP-1 and RARα expression in the epidermis of photoaged skin following application of this formulation, this supports its suitability for use in the treatment of aged skin.

Additionally, the following non-quantitative observations were made during the course of the trial relating to the effectiveness of ultrasound-based skin treatments. Although not directly comparable due to the protocol structuring of the trial, Topical 1 formulation applied with ultrasound appeared to induce a similar level of fibrillin to the retinoid formulation. Topical 1 formulation only and Topical 1 formulation applied with ultrasound did not induce erythema or epidermal hyperplasia, unlike the retinoid formulation. The degree of scarring at biopsy sites previously treated with ultrasound was noticeably lower than scarring at all other sites

REFERENCES

1. Watson REB, Griffiths C E M, Craven N M, Shuttleworth C A, Kielty C M. Fibrillin-rich microfibrils are reduced in photoaged skin: Distribution at the dermo-epidermal junction. *J Invest Dermatol*, 112: 782-787, 1999
2. Watson R E B, Craven N M, Kang S, Jones C J P, Kielty C M, Griffiths C E M. A short term screening protocol, using fibrillin-1 as a receptor molecule for photoageing repair agents. *J Invest Dermatol*, 116:672-678, 2001
3. Brennan M, Bhatti H, Nerusu K C, Bhagavathula N, Kang S, Fisher G J, Varani J, Voorhees J J. Matrix metalloproteinase-1 is the major collagenolytic enzyme responsible for collagen damage in UV-irradiated human skin. Photochem *Photobiol*, 78:43-48, 2003
4. Watson REB, Ratnayaka J A, Brooke R C, Yee-Sit-Yu S, Ancian P, Griffiths C E M. Retinoic acid receptor alpha expression and cutaneous ageing. Mech Ageing Dev, 125:465-473, 2004
5. Jantschitsch C, Trautinger F. Heat shock and UV-B-induced DNA damage and mutagenesis in skin. *Photochem Photobiol Sci*. 2:899-903, 2003
6. Debure L, Vayssiere J L, Rincheval V, Loison. F, Le Drean Y, Michel D. Intracellular clusterin causes juxtanuclear aggregate formation and mitochondrial alteration. *J Cell Sci.* 116:3109-3121, 2003

I claim:

1. A method for the application of ultrasound to the skin for the treatment of a dermatologic skin condition, comprising:
    applying to the skin a gel pad, gel cartridge or free flowing gel comprising a composition that includes one or more hyaluronan; and
    applying ultrasound directly or indirectly to an area of the skin where the gel pad, gel cartridge or free flowing gel has been applied, or as a pre-treatment to an area of the skin to which the gel pad, gel cartridge or free flowing gel is to be applied, wherein the ultrasound is applied using a plurality of dual frequency transducers each of which comprises a low frequency transducer element that delivers low frequency ultrasound in the range of 20 kHz to 500 kHz and a high frequency transducer element that is different from the low frequency transducer element and delivers high frequency ultrasound in the range of 0.5 MHz to 3.5 MHz, wherein the spatial average power density of the low frequency ultrasound energy is from 20 to 500 mW/cm$^2$, wherein the dual frequency transducers are driven in accordance with a treatment protocol for a dermatologic skin condition so as to deliver a desired sequence of low and high frequency ultrasound to the skin under treatment whereby an ultrasound field moves across the ultrasound transducer elements in a preset pattern and at a preset speed to treat the dermatologic skin condition.

2. The method of claim 1, wherein the method is a method of cosmetic treatment.

3. The method of claim 1, wherein the low frequency ultrasound and the high frequency ultrasound are applied simultaneously.

4. The method of claim 1, wherein the dual frequency transducers are arranged as an array in a flexible material in spaced configuration.

5. The method of claim 1, wherein the composition comprises both a low molecular weight hyaluronan having a molecular weight of less than $1\times10^6$ Da and a high molecular weight hyaluronan having a molecular weight of greater than $1\times10^6$ Da.

6. The method of claim 1, wherein the composition further comprises an anti-glycation agent, and wherein the anti-glycation agent is selected from the group consisting of one or more of alanyl-L-histidine (L-carnosine), N-acetylcysteine, aminoguanidine, D-penicillamine, acetylsalicyclic acid (aspirin), paracetamol, indomethacin and ibuprofen and/or a functional derivative or prodrug thereof.

7. The method of claim 1, wherein the composition further comprises an anti-glycation agent selected from the group consisting of one or more of beta-alanylhistamine (carcinine), N-acetyl-beta-alanylhistamine (N-acetyl carcinine), L-prolyl histamine, and/or N-acetyl-L-carnosine.

8. The method of claim 1, wherein the composition further comprises an anti-oxidant, and wherein the anti-oxidant is selected from the group consisting of one or more of arginine, ascorbic acid, a prodrug or derivative of ascorbic acid, ascorbyl palmitate, magnesium ascorbyl phosphate, trisodium ascorbyl phosphate, anserine, carnosine, opidine, homocarnosine and/or acetylanserine.

9. The method of claim 1, wherein the composition further comprises ascorbic acid, and wherein depolymerization of the hyaluronan is encouraged by the ascorbic acid.

10. The method of claim 1, wherein the composition comprises hyaluronan and ascorbic acid in a hydrogel in the form of a gel pad.

11. A kit comprising an ultrasound apparatus and a gel pad, gel cartridge or free flowing gel, wherein the gel pad, gel cartridge or free flowing gel comprises a composition that includes one or more hyaluronan, wherein the ultrasound apparatus comprises a plurality of dual frequency transducers each of which comprises a low frequency transducer element that delivers low frequency ultrasound of 20 kHz to 500 kHz and a high frequency transducer element that is different from the low frequency transducer element and delivers high frequency ultrasound of 0.5 MHz to 3.5 MHz directly or indirectly to an area of skin where the gel pad, gel cartridge or free flowing gel has been applied, or as a pre-treatment to an area of skin to which the gel pad, gel cartridge or free flowing gel is to be applied, wherein the spatial average power density of the low frequency ultrasound energy is from 20 to 500 mW/cm$^2$, and wherein the ultrasound apparatus further comprises a drive circuit operable to drive the dual frequency transducers in accordance with a treatment protocol for a dermatologic skin condition so as to deliver a desired sequence of low and high frequency ultrasound to the skin under treatment whereby an ultrasound field moves across the dual frequency transducers in a preset pattern and at a preset speed to treat the dermatologic skin condition.

12. The kit of claim 11, wherein the composition comprises both a low molecular weight hyaluronan having a molecular weight of less than 1×10$^6$ Da and a high molecular weight hyaluronan having a molecular weight of greater than 1×10$^6$ Da.

13. The kit of claim 11, wherein the composition further comprises an anti-glycation agent, and wherein the anti-glycation agent is selected from the group consisting of one or more of alanyl-L-histidine (L-carnosine), N-acetylcysteine, aminoguanidine, D-penicillamine, acetylsalicyclic acid (aspirin), paracetamol, indomethacin and ibuprofen and/or a functional derivative or prodrug thereof.

14. The kit of claim 11, wherein the composition further comprises an anti-glycation agent selected from the group consisting of one or more of beta-alanylhistamine (carcinine), N-acetyl-beta-alanylhistamine (N-acetylcarcinine), L-prolyl histamine, and/or N-acetyl-L-carnosine.

15. The kit of claim 11, wherein the composition further comprises an anti-oxidant, and wherein the anti-oxidant is selected from the group consisting of one or more of arginine, ascorbic acid, a prodrug or derivative of ascorbic acid, ascorbyl palmitate, magnesium ascorbyl phosphate, trisodium ascorbyl phosphate, anserine, carnosine, opidine, homocarnosine and/or acetylanserine.

16. The kit of claim 11, wherein the composition comprises hyaluronan and ascorbic acid in a hydrogel in the form of a gel pad.

17. The kit of claim 11, wherein the dual frequency transducers are arranged as an array in a flexible material in spaced configuration.

18. The kit of claim 17, wherein each of the dual frequency transducers is capable of delivering low and high frequency ultrasound simultaneously or sequentially.

19. The kit of claim 17, wherein each of the dual frequency transducers is capable of delivering low and high frequency ultrasound along a common axis.

20. The kit of claim 17, wherein each of the dual frequency transducers is capable of delivering ultrasound in a pulsed mode or a continuous mode.

21. The kit of claim 17, wherein the array of dual frequency transducers is controllable.

22. The kit of claim 11, wherein the preset pattern comprises one or more of: movement from left to right or vice versa across a full width of the array; movement up and down the array; and movement into the center of the array and then out again.

23. The kit of claim 17, further comprising an ultrasound generator.

24. The kit of claim 23, wherein each of the dual frequency transducers is individually connected to the ultrasound generator.

25. The kit of claim 17, wherein each of the dual frequency transducers is capable of delivering low frequency ultrasound at a frequency of 50 kHz.

26. The kit of claim 17, wherein each of the dual frequency transducers is capable of delivering high frequency ultrasound at a frequency in the range of 1 MHz to 3 MHz.

27. The kit of claim 17, wherein the spatial average power density of the high frequency ultrasound energy is from 0.5 to 3 W/cm$^2$.

28. The kit of claim 17, wherein the array of dual frequency transducers is programmable so as to deliver the desired sequence of low and high frequency ultrasound to the skin under treatment.

* * * * *